(12) United States Patent
Park et al.

(10) Patent No.: US 10,966,685 B2
(45) Date of Patent: Apr. 6, 2021

(54) METHOD AND ULTRASOUND APPARATUS FOR PROVIDING ULTRASOUND ELASTOGRAPHY IMAGE

(71) Applicant: Samsung Electronics Co., Ltd., Suwon (KR)

(72) Inventors: Ji-young Park, Yongin (KR); Jun-ho Park, Hwaseong (KR); Ki-wan Choi, Anyang (KR); Hyoung-ki Lee, Seongnam (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 669 days.

(21) Appl. No.: 14/499,805

(22) Filed: Sep. 29, 2014

(65) Prior Publication Data
US 2015/0148674 A1    May 28, 2015

(30) Foreign Application Priority Data
Nov. 28, 2013   (KR) .......................... 10-2013-0146443

(51) Int. Cl.
*A61B 8/00* (2006.01)
*A61B 8/08* (2006.01)
*A61B 8/14* (2006.01)

(52) U.S. Cl.
CPC .............. *A61B 8/485* (2013.01); *A61B 8/085* (2013.01); *A61B 8/4245* (2013.01); *A61B 8/463* (2013.01); *A61B 8/469* (2013.01); *A61B 8/54* (2013.01); *A61B 8/5246* (2013.01); *A61B 8/5292* (2013.01)

(58) Field of Classification Search
CPC ....... A61B 8/485; A61B 8/085; A61B 8/4145; A61B 8/463; A61B 8/469; A61B 8/54
See application file for complete search history.

(56) References Cited

U.S. PATENT DOCUMENTS

| 6,544,179 | B1 | 4/2003 | Schmiesing et al. |
| 8,187,187 | B2 | 5/2012 | Fan et al. |
| 8,500,639 | B2 | 8/2013 | Yao |
| 2009/0304250 | A1 | 12/2009 | McDermott et al. |

(Continued)

FOREIGN PATENT DOCUMENTS

| JP | 2009-552 | 1/2009 |
| KR | 10-2015-0011275 | 1/2015 |

(Continued)

OTHER PUBLICATIONS

Extended European Search Report dated Jun. 11, 2015 in corresponding European Patent Application No. 14192942.2.

(Continued)

*Primary Examiner* — Katherine L Fernandez
*Assistant Examiner* — Colin T. Sakamoto
(74) *Attorney, Agent, or Firm* — Staas & Halsey LLP

(57) ABSTRACT

A method of providing an ultrasound elastography image that includes inducing a shear wave by transmitting a first ultrasound signal pushing an object to the object, transmitting a second ultrasound signal tracing the shear wave to the object to receive a response signal to the second ultrasound signal from the object; acquiring an elastography image of the object, based on the response signal, and providing the elastography image of the object and transmission position information of the first ultrasound signal.

9 Claims, 19 Drawing Sheets

(56) References Cited

U.S. PATENT DOCUMENTS

| | | | |
|---|---|---|---|
| 2010/0010348 A1* | 1/2010 | Halmann | A61B 8/00 600/443 |
| 2010/0069751 A1 | 3/2010 | Hazard et al. | |
| 2010/0160781 A1* | 6/2010 | Carter | A61B 8/06 600/439 |
| 2010/0286520 A1 | 11/2010 | Hazard et al. | |
| 2012/0136250 A1* | 5/2012 | Tabaru | G01S 7/52026 600/438 |
| 2013/0218012 A1* | 8/2013 | Specht | A61B 8/485 600/438 |
| 2014/0046173 A1* | 2/2014 | Greenleaf | G01N 29/075 600/411 |

FOREIGN PATENT DOCUMENTS

| | | |
|---|---|---|
| WO | 2011/001333 A1 | 1/2011 |
| WO | WO 2011/001776 | 1/2011 |
| WO | 2012/080913 A1 | 6/2012 |

OTHER PUBLICATIONS

Korean Notice of Allowance dated May 31, 2016 in corresponding Korean Patent Application No. 10-2013-0146443.

* cited by examiner

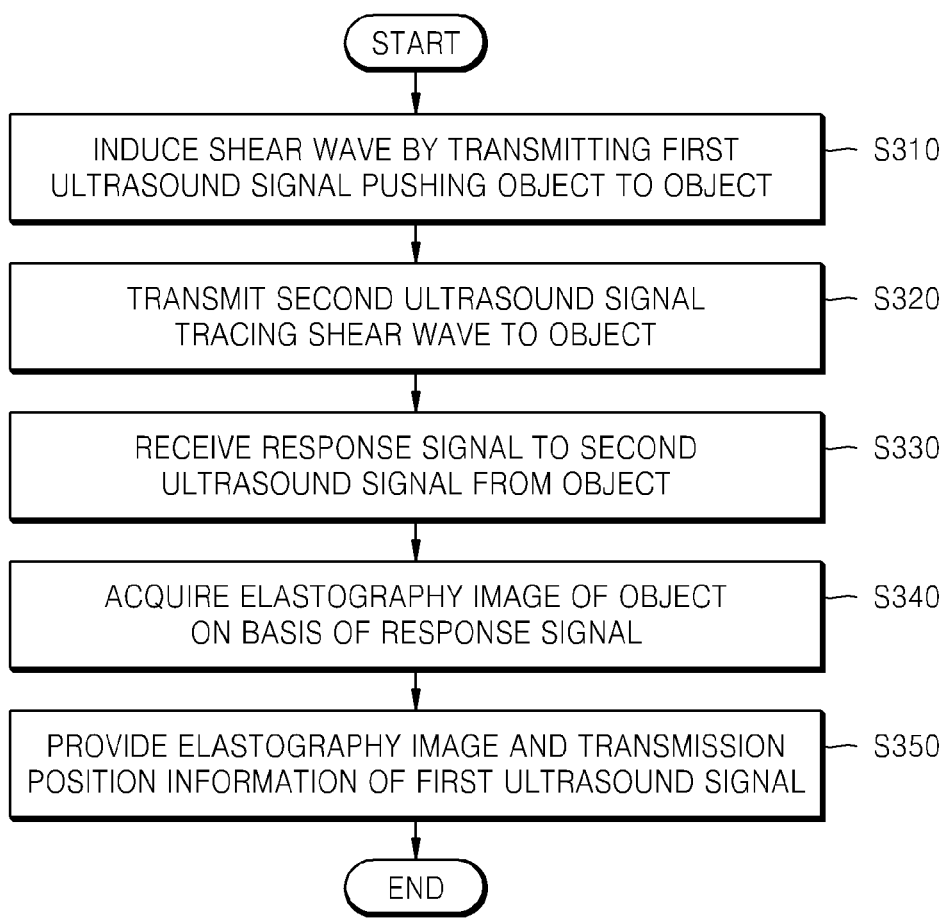

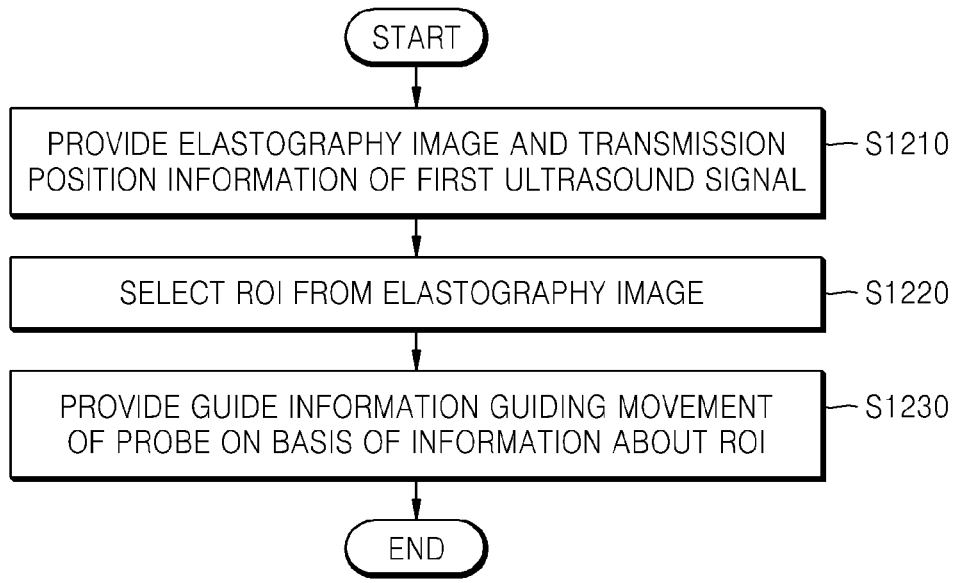
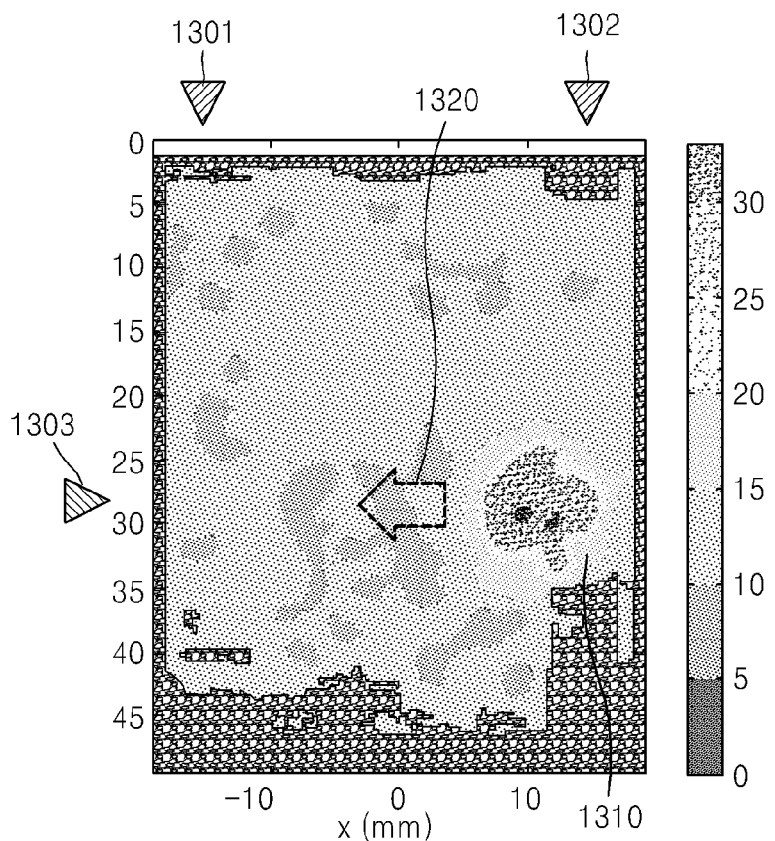

METHOD AND ULTRASOUND APPARATUS FOR PROVIDING ULTRASOUND ELASTOGRAPHY IMAGE

RELATED APPLICATIONS

This application claims the benefit of Korean Patent Application No. 10-2013-0146443, filed on Nov. 28, 2013, in the Korean Intellectual Property Office, the disclosure of which is incorporated herein in its entirety by reference.

BACKGROUND

1. Field

One or more embodiments relate to a method and ultrasound apparatus for providing an ultrasound elastography image using a shear wave.

2. Description of the Related Art

Ultrasound diagnostic apparatuses transfer an ultrasound signal from a surface of an object to a certain part of a human body, and obtain a tomography image of a soft tissue or an image of a blood flow by using information of an ultrasound signal reflected from an internal tissue of the human body.

Ultrasound diagnostic apparatuses are small and inexpensive, and display an acquired image in real time. Also, ultrasound diagnostic apparatuses have a high stability because an object is not exposed to X-ray or the like, and thus are being widely used along with other image diagnostic apparatuses, such as X-ray diagnostic apparatuses, computerized tomography (CT) scanners, magnetic resonance imaging (MRI) apparatuses, and nuclear medicine diagnostic apparatuses.

An elastography method displays an elasticity of an object as an image. An elasticity of an object is relevant to a pathologic phenomenon of the object. A tumor is harder than normal tissue. That is, an elasticity of tumor is greater than that of a normal tissue, and thus, when the same pressure is applied to the tumor and the normal tissue, a strain of the normal tissue is greater than that of the tumor. Therefore, the elastography method may be used to diagnose a tumor or cancer.

For example, an elasticity contrast index (ECI) acquired by the elastography method may be used to diagnose a nodule of a tissue. The ECI is obtained by quantifying a hardness difference between a nodule of a tissue and a normal tissue near the nodule. As the ECI increases, the nodule is hard, and a probability that the nodule is malignant increases. Also, the elastography method may be applied to various fields such as monitoring of a kidney transplant, skin and tissue engineering, monitoring of cancer treatment, etc., in addition to detection and classification of cancer or tumor.

As the elastography method, a free-hand elastography method is being most widely used. The free-hand elastography method is a method in which a user directly applies a pressure by using a probe, and is simple in use. However, the free-hand elastography method has a drawback in that a pressure cannot equally be applied.

Therefore, an ultrasound apparatus that solves the drawback of the free-hand elastography method and provides accurate elastography is needed.

SUMMARY

One or more embodiments include a method and ultrasound apparatus for providing an ultrasound elastography image, which provide an elastography image of an object and transmission position (or a generation position of a shear wave) information of an ultrasound signal (an ultrasound push beam) used to push the object.

One or more embodiments include a method and ultrasound apparatus for providing an ultrasound elastography image, which change a transmission position of an ultrasound signal used to push an object on the basis of a user input or a region of interest (ROI), thereby increasing an accuracy of an elastography image.

Additional aspects will be set forth in part in the description which follows and, in part, will be apparent from the description, or may be learned by practice of the presented embodiments.

According to one or more embodiments, a method of providing an ultrasound elastography includes: inducing a shear wave by transmitting a first ultrasound signal pushing an object into the object; transmitting a second ultrasound signal tracing the shear wave to the object, and receiving a response signal to the second ultrasound signal from the object; acquiring an elastography image of the object, based on the response signal; and providing the elastography image of the object and transmission position information of the first ultrasound signal.

The providing may include displaying at least one indicator, indicating a transmission position of the first ultrasound signal, on the elastography image.

The method may further include: receiving a user input that changes a position of the at least one indicator; and changing the transmission position of the first ultrasound signal, based on the user input.

The method may further include: when the transmission position of the first ultrasound signal is changed, acquiring a new elastography image of the object; and displaying the new elastography image and information about the changed transmission position of the first ultrasound signal.

The method may further include: selecting a region of interest (ROI) from the elastography image; changing the transmission position of the first ultrasound signal, based on the selected ROI; acquiring a new elastography image of the object; and displaying the new elastography image and information about the changed transmission position of the first ultrasound signal.

The selecting of a region of interest may include selecting the ROI from the elastography image, based on a user input.

The changing of the transmission position may include changing the transmission position of the first ultrasound signal so that the first ultrasound signal is transmitted to a region other than the ROI of the object.

The ROI may include at least one of a cystis image and a tumor image.

The method may further include: selecting a region of interest (ROI) from the elastography image; and providing guide information that guides a movement of a probe, based on the information about the ROI.

The method may further include providing information about a focal depth of the first ultrasound signal.

The method may further include: displaying at least one indicator, indicating the focal depth of the first ultrasound signal, on the elastography image; receiving a user input that changes a position of the at least one indicator; and adjusting the focal depth of the first ultrasound signal, based on the user input.

The method may further include: extracting an alert zone of the elastography image in which an accuracy of an elasticity value is less than a threshold value, based on the transmission position information of a first ultrasound signal; and displaying information about the alert zone.

According to one or more embodiments, an apparatus for providing an ultrasound elastography image includes: a probe that transmits a first ultrasound signal pushing an object into the object to induce a shear wave, transmits a second ultrasound signal tracing the shear wave to the object, and receives a response signal to the second ultrasound signal from the object; a control unit that acquires an elastography image of the object, based on the response signal; and a display unit that provides the elastography image of the object and transmission position information of the first ultrasound signal.

The display unit may display at least one indicator, indicating a transmission position of the first ultrasound signal, on the elastography image.

The apparatus may further include a user input unit that receiving a user input that changes a position of the at least one indicator, wherein the control unit may change the transmission position of the first ultrasound signal, based on the user input.

When the transmission position of the first ultrasound signal is changed, the control unit may acquire a new elastography image of the object, and the display unit may display the new elastography image and information about the changed transmission position of the first ultrasound signal.

The control unit may select a region of interest (ROI) from the elastography image, changes the transmission position of the first ultrasound signal, based on the selected ROI, and acquires a new elastography image of the object, and the display unit may display the new elastography image and information about the changed transmission position of the first ultrasound signal.

The control unit may select the ROI from the elastography image, based on a user input.

The control unit may change the transmission position of the first ultrasound signal so that the first ultrasound signal is transmitted to a region other than the ROI of the object.

The control unit may select a region of interest (ROI) from the elastography image, and provides guide information that guides a movement of a probe, based on the information about the ROI.

The display unit may further provide information about a focal depth of the first ultrasound signal.

The display unit may display at least one indicator, indicating the focal depth of the first ultrasound signal, on the elastography image, and the control unit may receive a user input that changes a position of the at least one indicator, and adjusts the focal depth of the first ultrasound signal, based on the user input.

The control unit may extract an alert zone of the elastography image in which an accuracy of an elasticity value is less than a threshold value, based on the transmission position information of a first ultrasound signal, and controls the display unit to display information about the alert zone.

According to one or more embodiments a includes transmitting a push ultrasound beam into an object at a beam position, transmitting a trace ultrasound signal into the object tracing a shear wave produced by the push ultrasound beam, and producing an image from a trace ultrasound response signal from the object, where the transmitting transmits the push ultrasound beam at another beam position. The another beam position may be determined by a user moving a beam position indicator on the image or the another beam position may be determined by a user specified region of interest designated on the image by the user or the another beam position may be determined using shear modulus to specify a region of interest. The beam position may be adjusted by using different channel groups of a fixed position transducer. The image may show shear modulus within the object and the beam position and beam direction allowing a user to see if a region of interest may be on a path of the push ultrasound beam where the image may be compromised because a shear wave may not be induced. The image may show a focal depth of the push ultrasound beam

BRIEF DESCRIPTION OF THE DRAWINGS

These and/or other aspects will become apparent and more readily appreciated from the following description of the embodiments, taken in conjunction with the accompanying drawings in which:

FIG. 3 is a flowchart for describing a method of providing an ultrasound elastography image according to an embodiment;

FIG. 12 is a flowchart for describing a method of providing guide information which guides a movement of a probe, according to an embodiment;

FIG. 13 is a diagram illustrating an example of a guide image which guides a movement of a probe;

DETAILED DESCRIPTION

Figure 1:
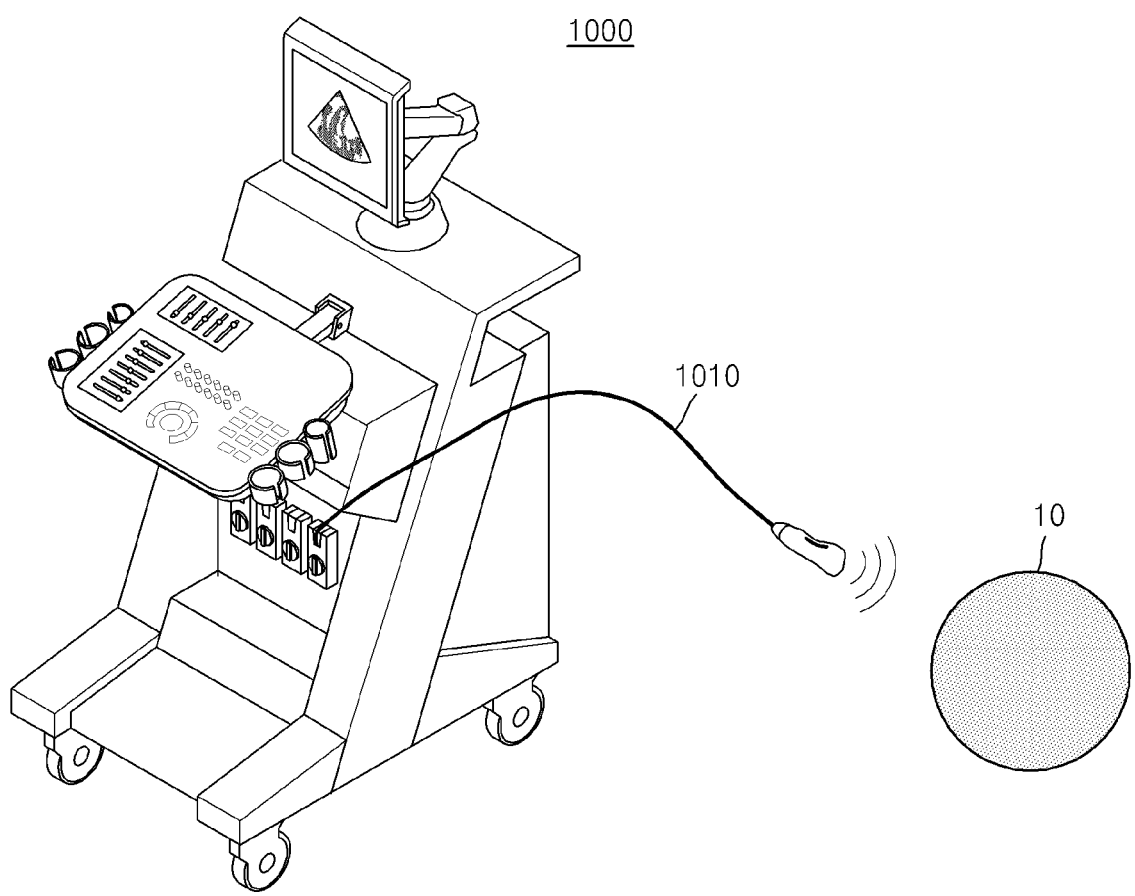
FIG. 1 is a diagram illustrating an ultrasound apparatus according to an embodiment.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. Expressions such as "at least one of," when preceding a list of elements, modify the entire list of elements and do not modify the individual elements of the list.

Hereinafter, the terms used in the specification will be briefly described, and then will be described in detail.

The terms used in this specification are those general terms currently widely used in the art in consideration, but the terms may vary according to the intention of those of ordinary skill in the art, precedents, or new technology in the art. Also, specified terms may be selected by the applicant, and in this case, the detailed meaning thereof will be described in the detailed description. Thus, the terms used in the specification should be understood not as simple names but based on the meaning of the terms and the overall description.

Throughout the specification, it will also be understood that when a component "includes" an element, unless there is another opposite description thereto, it should be understood that the component does not exclude another element but may further include another element. In addition, terms such as " . . . unit", " . . . module", or the like refer to units that perform at least one function or operation, and the units may be implemented as hardware or software or as a combination of hardware and software.

Throughout the specification, an "ultrasonic image" refers to an image of an object obtained using an ultrasonic wave. Furthermore, in the present specification, "object" may include a person or an animal, or a part of a person or an animal. For example, the object may include the liver, the heart, the womb, the brain, a breast, the abdomen, or a blood vessel. Furthermore, the "object" may include a phantom. The phantom means a material having a volume that is approximately the intensity and effective atomic number of a living thing, and may include a sphere phantom having a property similar to a human body.

Furthermore, in the present specification, "user" refers to a medical professional, such as a doctor, a nurse, a medical laboratory technologist, and an engineer who repairs a medical apparatus, but the user is not limited thereto.

Reference will now be made in detail to embodiments, examples of which are illustrated in the accompanying drawings. In this regard, the present embodiments may have different forms and should not be construed as being limited to the descriptions set forth herein. In the following description, well-known functions or constructions are not described in detail since they would obscure the embodiments with unnecessary detail.

FIG. 1 is a diagram illustrating an ultrasound apparatus 1000 according to an embodiment.

As illustrated in FIG. 1, the ultrasound apparatus 1000 may transmit an ultrasound signal to an object 10 through a probe 1010. The ultrasound apparatus 1000 may receive an ultrasound echo signal reflected from the object 10 to generate an ultrasound image.

In the present specification, an ultrasound image may be variously implemented. For example, the ultrasonic image may include at least one of a brightness (B) mode image in which a level of an ultrasonic echo signal reflected from an object is expressed as brightness, a color Doppler image in which a speed of a moving object is expressed as a color by using the Doppler effect, a spectral Doppler image in which an image of a moving object is expressed as a spectrum type by using the Doppler effect, and a motion (M) mode image that shows a motion of an object with time at a certain place, but is not limited thereto. According to an embodiment, the ultrasound may be a two-dimensional (2D) image, a three-dimensional (3D) image, or a fourth-dimensional (4D) image.

According to an embodiment, the ultrasound apparatus 1000 may provide an elastography image that shows an elasticity contrast of the object as an image by using acoustic radiation force. This will be described in detail with reference to FIGS. 2A and 2B.

Figure 2A:
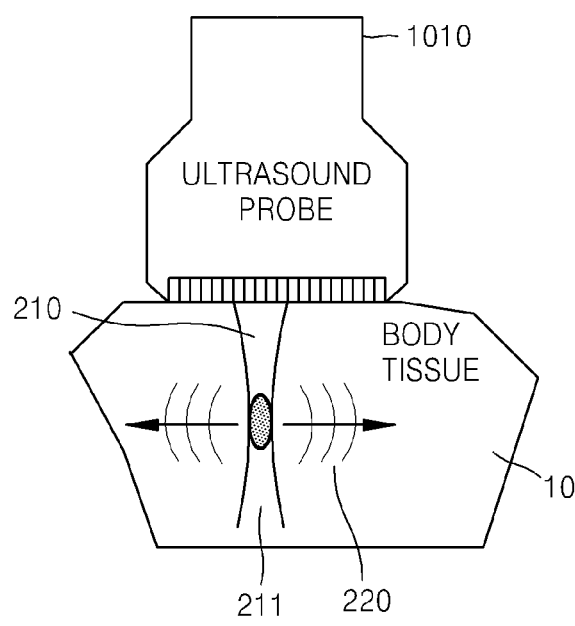
FIGS. 2A and 2B are diagrams for describing a shear wave generated in an object.
Figure 2B:
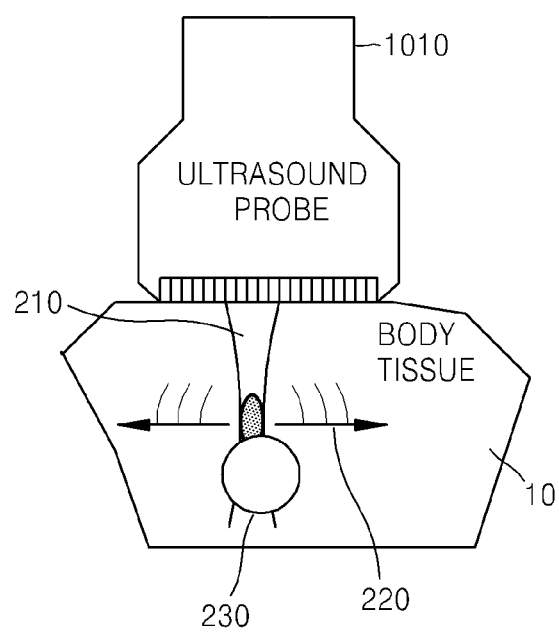

FIGS. 2A and 2B are diagrams for describing a shear wave generated in an object.

As illustrated in FIG. 2A, the ultrasound apparatus 1000 may transmit an ultrasound signal (for convenience of description, hereinafter referred to as a push ultrasound signal) or ultrasound push beam, used to push a partial region of the object 10, to the object 10. For example, the ultrasound apparatus 1000 may transmit a push ultrasound signal 210 having a long wavelength to or into the object 10 by using thirty to forty channels of the probe 1010. According to an embodiment, the ultrasound apparatus 1000 may transmit the focused push ultrasound signal 210 to a partial region of the object 10.

In this case, a shear wave 220 may be generated from the push ultrasound signal 210 by the inside of the object 10. For example, the shear wave 220 may be generated with respect to a region pushed by the push ultrasound signal 210. The shear wave 220 may have a speed of about 1 m/s to about 10 m/s. The speed (for example, about 1 m/s to about 10 m/s) of the shear wave 220 is far lower than an average speed (i.e., about 1540 m/s) of an ultrasound signal in the object 10, and thus, the ultrasound apparatus 1000 may use a general ultrasound signal (hereinafter referred to as a trace ultrasound signal) for tracing the shear wave 220. For example, the ultrasound apparatus 1000 may transmit the trace ultrasound signal in a traveling direction of the shear wave 220, thereby tracing the speed of the shear wave 220. Here, a wavelength of the trace ultrasound signal may be shorter than that of the push ultrasound signal 210.

The shear wave 220 is induced in a direction vertical (or perpendicular) to a traveling direction of the focused push ultrasound signal 210, and thus, the shear wave 220 may not be induced in a region 211 of the object 10 in which the focused push ultrasound signal 210 travels and the image may be compromised in the path.

As illustrated in FIG. 2B, the push ultrasound signal 210 cannot pass through hard objects such as a cystis 230, bones, etc. For example, when the probe 1010 transmits the push ultrasound signal 210 to a region having the cystis 230, the shear wave 220 is not normally generated, and for this reason, an inaccurate elastography image of the object 10 is or may be acquired.

A method, in which the ultrasound apparatus 1000 provides information about a transmission position of the push ultrasound signal 210 so that a user changes the transmission position of the push ultrasound signal 210 to obtain an accurate elastography image of an ROI, will be described below in detail with reference to FIG. 3. Hereinafter, for convenience of description, the push ultrasound signal 210 is referred to as a first ultrasound signal, and the trace ultrasound signal is referred to as a second ultrasound signal.

FIG. 3 is a flowchart for describing a method of providing an ultrasound elastography image according to an embodiment.

In operation S310, the ultrasound apparatus 1000 may transmit a first ultrasound signal, used to push an object, to or into the object. According to an embodiment, the first ultrasound signal may be a focused long-wavelength ultrasound signal. According to an embodiment, a shear wave may be induced with respect to a pushed position of the object. The shear wave may move in both directions vertical or perpendicular to a traveling direction of the first ultrasound signal. The shear wave may move at a speed of about 1 m/s to about 10 m/s.

When a position of the probe 1010 is fixed, the first ultrasound signal may be transmitted from one position of the probe 1010, and a plurality of the first ultrasound signals may be sequentially transmitted from a plurality of positions of the probe 1010. That is, according to an embodiment, one or more regions of the object may be pushed.

For example, by using a first channel group of the probe 1010, the ultrasound apparatus 1000 may transmit the first ultrasound signal to the object to generate a first shear wave. Also, by sequentially using the first channel group and a second channel group of the probe 1010, the ultrasound apparatus 1000 may transmit the first ultrasound signal a plurality of times to generate the first shear wave and a second shear wave.

In operation S320, the ultrasound apparatus 1000 may transmit the second ultrasound signal, used to trace a shear wave, to the object. For example, the ultrasound apparatus 1000 may transmit the second ultrasound signal to a region of the object to or into which the shear wave is propagated. According to an embodiment, the second ultrasound signal may be transmitted to the object through all channels of the probe 1010.

In operation S330, the ultrasound apparatus 1000 may receive a response signal to the second ultrasound signal from the object. The response signal may be a signal reflected from the object.

In operation S340, the ultrasound apparatus 1000 may acquire an elastography image of the object on the basis of the response signal. For example, the ultrasound apparatus 1000 may analyze a shear-wave speed in each region of the object by using the response signal. The ultrasound apparatus 1000 may generate an elastography image by using the shear-wave speed.

Generally, the shear-wave speed and a degree of elasticity may have a proportional relationship. That is, the shear-wave speed may be faster in tumor in which the degree of elasticity is greater than that of a normal tissue. The ultrasound apparatus 1000 may map the shear-wave speed to a color, or map a shear modulus to a color, thereby generating an elastography image.

In operation S350, the ultrasound apparatus 1000 may provide an elastography image of the object and transmission position information of the first ultrasound signal.

According to an embodiment, the ultrasound apparatus 1000 may display a B mode image to overlap on the elastography image. In this case, the ultrasound apparatus 1000 may display the elastography image on the B mode image in a semi-transmissive state.

According to an embodiment, the ultrasound apparatus 1000 may perform transparency processing of a region in which an elasticity value is not calculated in the elastography image. For example, the shear wave is not generated in a region under a portion of the object pushed by the ultrasound signal, and thus, the elasticity value is not normally calculated. Also, since the first ultrasound signal cannot pass through a hard region such as a cystis or a bone, the elasticity value is not normally calculated in a region near a cystis or a bone.

When the ultrasound apparatus 1000 performs transparency processing of a first region in which the elasticity value is not calculated in a state where the B mode image overlaps the elastography image, only the B mode image may be displayed in the first region in which the elasticity value is not calculated, and a second region in which the elasticity value is calculated may be displayed as a color value.

According to an embodiment, the ultrasound apparatus 1000 may provide transmission position information of the first ultrasound signal. According to an embodiment, the transmission position information of the first ultrasound signal is information about which region of the object the first ultrasound signal is transmitted to, and may include information about a pushed region and information about a generation position of a shear wave.

According to an embodiment, the ultrasound apparatus 1000 may display at least one indicator, indicating the transmission position of the first ultrasound signal, on the elastography image. Here, the at least one indicator indicating the transmission position of the first ultrasound signal may be expressed as various types. For example, the indicator may be displayed as an arrow, a line, a box, a circle, or the like, but is not limited thereto.

According to an embodiment, the ultrasound apparatus 1000 may provide information about a focal depth of the first ultrasound signal. The information about the focal depth may include focal distance information, focal region information, etc., but is not limited thereto. This will be described below in detail with reference to FIG. 15.

Figure 4A:
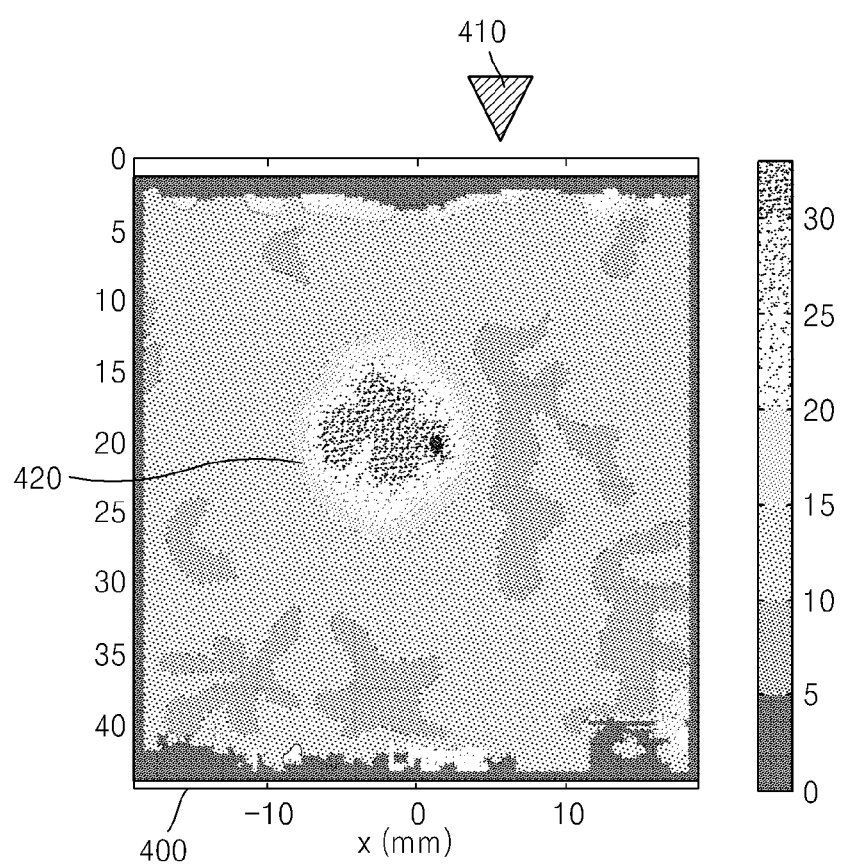
FIGS. 4A and 4B are diagrams for describing transmission position information of a first ultrasound signal according to an embodiment.
Figure 4B:
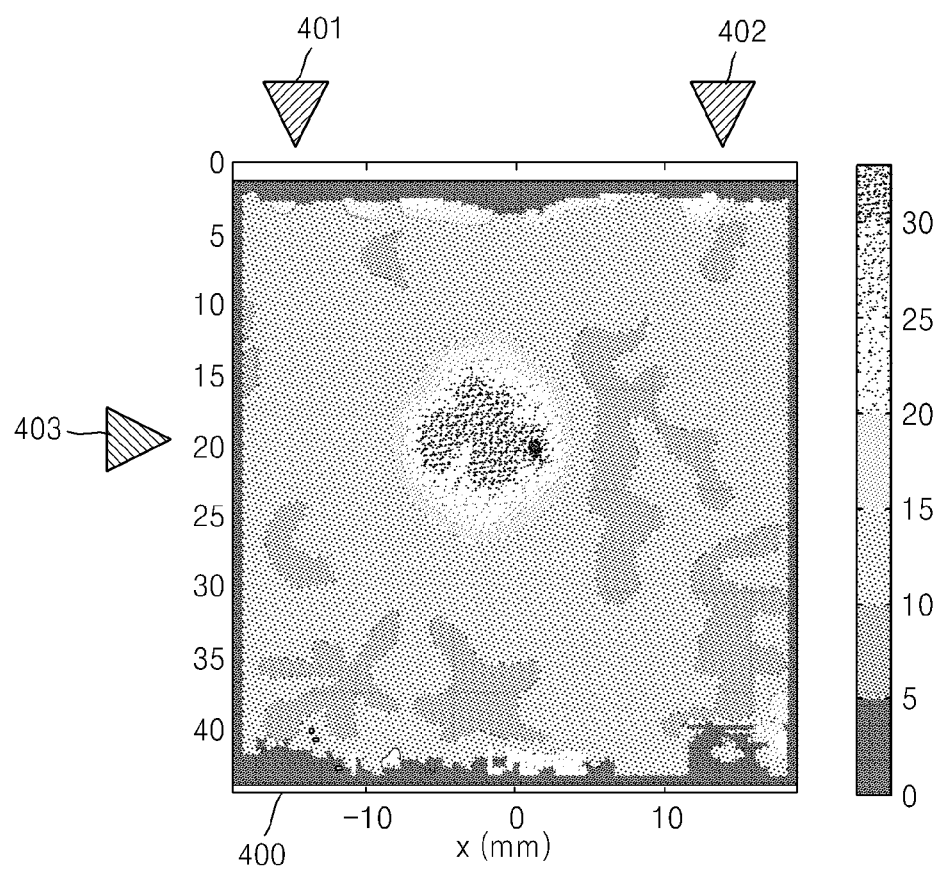

FIGS. 4A and 4B are diagrams for describing transmission position information of a first ultrasound signal (a push ultrasound signal or beam) according to an embodiment.

As illustrated in FIG. 4A, the ultrasound apparatus 1000 may display an indicator 410 indicating the transmission position (and direction) of the first ultrasound signal, along with an elastography image 400.

For example, the ultrasound apparatus 1000 may display a result, which is obtained by mapping the shear modulus (for example, about 0 to about 35) to a color value, as the elastography image 400. When the shear modulus is equal to or more than 25, a corresponding region may be displayed in red, and when the shear modulus is less than 10, a corresponding region may be displayed in blue. In this case, since the shear-wave speed of a region 420 having tumor is faster than that of a region having a normal tissue, the region 420 may have a high shear modulus. That is, the region 420 having tumor may be displayed in red.

Since the indicator 410 indicating the transmission position of the first ultrasound signal is displayed at the right of the region 420 having tumor, a user may check that tumor is not on a moving path (for example, under a pushed region) of the first ultrasound signal. Therefore, the user may determine that the elastography image of the region 420 having tumor is accurate and not compromised.

As illustrated in FIG. 4B, according to an embodiment, the ultrasound apparatus 1000 may transmit the first ultrasound signal from a first transmission position into an object to induce a first shear wave from the inside of the object, and may transmit the first ultrasound signal from a second transmission position (which differs from the first transmission position) into the object to induce a second shear wave from the inside of the object.

The first and second shear waves are all propagated to a region between the first and second transmission positions, and thus, an image of the region between the first and second transmission positions is most accurate in the elastography image 400.

According to an embodiment, the ultrasound apparatus 1000 may display a plurality of indicators indicating the transmission position of the first ultrasound signal. For example, the ultrasound apparatus 1000 may display a first indicator 401 indicating the first transmission position and a second indicator 402 indicating the second transmission position along with the elastography image 400.

According to an embodiment, the ultrasound apparatus 1000 may display at least one indicator 403, indicating a focal depth of the first ultrasound signal, along with the elastography image 400. This will be described below in detail with reference to FIG. 15.

Figure 5:
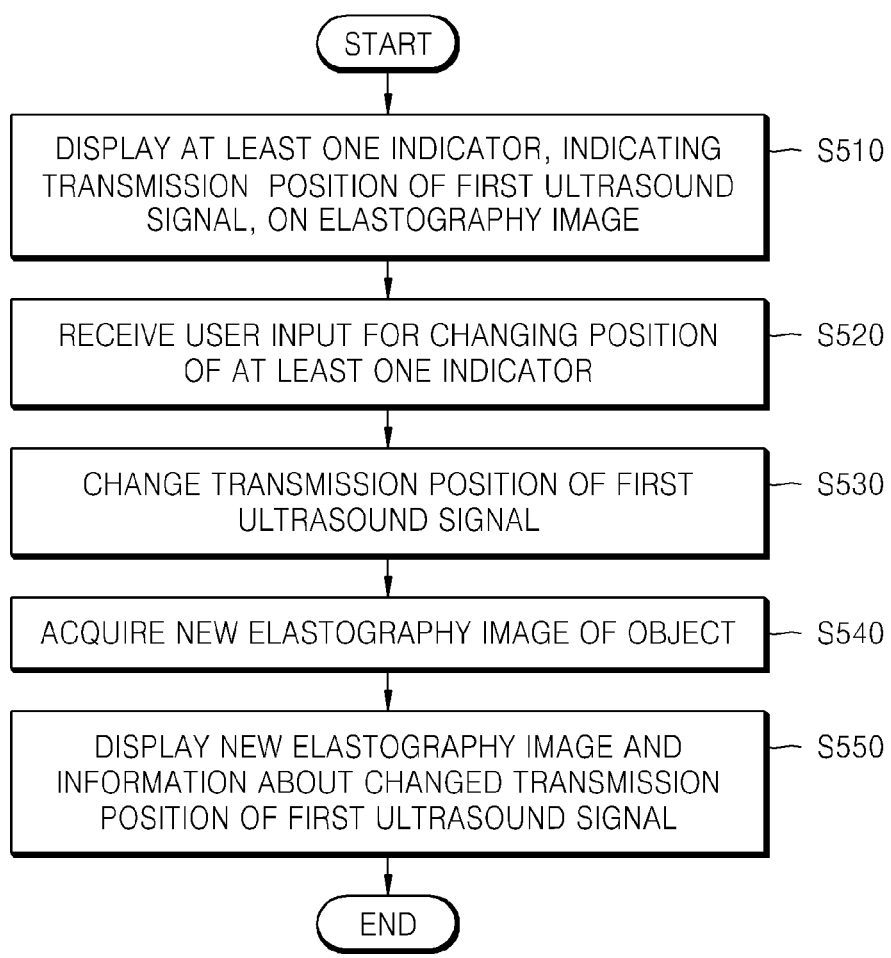
FIG. 5 is a flowchart for describing a method of changing a transmission position of a first ultrasound signal on the basis of a user input, according to an embodiment.

FIG. 5 is a flowchart for describing a method of changing a transmission position of a first ultrasound signal on the basis of a user input, according to an embodiment.

In operation S510, the ultrasound apparatus 1000 may display at least one indicator, indicating the transmission position of the first ultrasound signal, on an elastography image. In this case, a user may check the transmission position of the first ultrasound signal to determine an accuracy of an elastorgraphy of each region of an object. For example, the user may determine that an elastography image of a region on a moving path of the first ultrasound signal or an elastography image of a region under a generation position of a shear wave is low in accuracy, and an elastography image of a region between a generation position of a first shear wave and a generation position of a second shear wave is high in accuracy.

In operation S520, the ultrasound apparatus 1000 may receive a user input for changing a position of the at least one indicator. Here, the user input may be various. For example, the user input may include a key input, a touch input, a voice input, a motion input, and a multi-input, but is not limited thereto.

According to an embodiment, when tumor is in a region (for example, a region under the generation position of the first shear wave) corresponding to a first transmission position of the first ultrasound, the user may change a position of a first indicator indicating the first transmission position of the first ultrasound signal. For example, the user may move the first indicator to a region having no tumor.

According to an embodiment, the ultrasound apparatus 1000 may receive a user input for changing a position of one indicator, and receive a user input for changing positions of a plurality of indicators.

In operation S530, the ultrasound apparatus 1000 may change the transmission position of the first ultrasound signal on the basis of the user input.

For example, when a position of the probe 1010 on an object is fixed, the ultrasound apparatus 1000 may change a channel, through which the first ultrasound signal is transmitted, from the first channel group to the second channel group. Therefore, the user may move an indicator even without moving the probe 1010, thereby changing the transmission position of the first ultrasound signal.

In operation S540, the ultrasound apparatus 1000 may acquire a new elastography image of the object.

For example, the ultrasound apparatus 1000 may transmit the first ultrasound signal from a new transmission position to the object. In this case, a new shear wave may be generated from the first ultrasound signal at the new transmission position and in the object. The ultrasound apparatus 1000 may transmit a second ultrasound signal used to trace the newly generated shear wave. The ultrasound apparatus 1000 may receive a response signal to the second ultrasound signal, and generate a new elastography image by using the received response signal.

In operation S550, the ultrasound apparatus 1000 may display the new elastography image and information about the changed transmission position of the first ultrasound signal. The ultrasound apparatus 1000 may display the new elastography image to overlap on the B mode image. The ultrasound apparatus 1000 may display, on the new elastography image, the information about the changed transmission position of the first ultrasound signal. For example, the ultrasound apparatus 1000 may display an indicator, corresponding to the changed transmission position of the first ultrasound signal, near the new elastography image.

Figure 6:
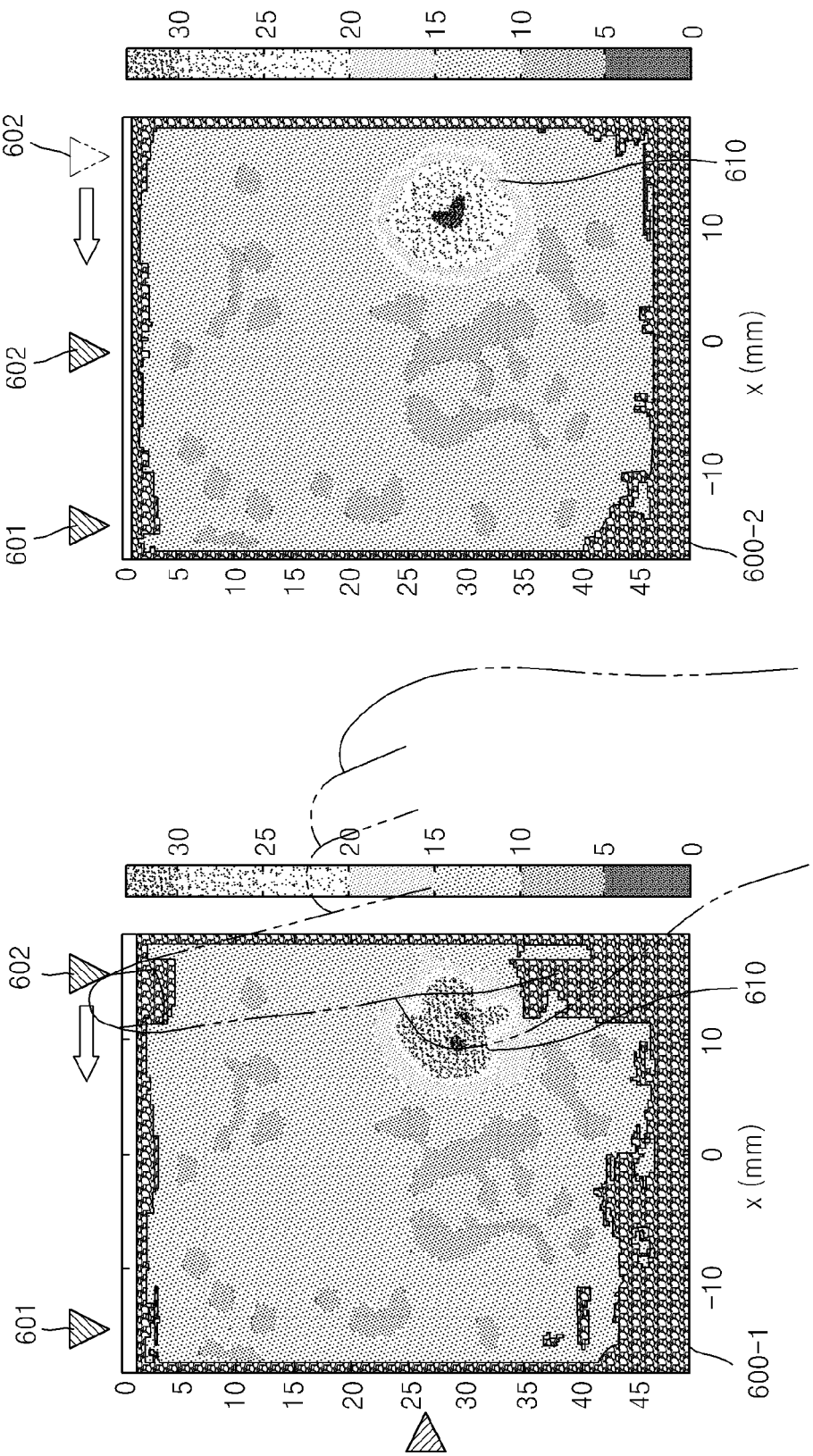
FIGS. 6A and 6B are diagrams illustrating a new elastography image corresponding to a changed transmission position of a first ultrasound signal, according to an embodiment.

FIGS. 6A and 6B are diagrams illustrating a new elastography image corresponding to a changed transmission position of a first ultrasound signal, according to an embodiment.

As illustrated in FIG. 6A, the ultrasound apparatus 1000 may sequentially transmit a first ultrasound signal (a push ultrasound signal) from first and second transmission positions. The ultrasound apparatus 1000 may trace a shear wave, which is generated from the first ultrasound signal, by using a second ultrasound signal (a trace ultrasound signal) to generate a first elastography image 600-1.

The ultrasound apparatus 1000 may display a first indicator 601 indicating the first transmission position of the first ultrasound signal and a second indicator 602 indicating the second transmission position of the first ultrasound signal along with the first elastography image 600-1.

In this case, since a region 610 which is suspected for a lesion is under the second indicator 602, a shear wave is not normally propagated to the lesion-suspected region 610. That is, an elastography image value of the lesion-suspected region 610 is not accurate. Therefore, a user may move the second indicator 602 in a left direction (using a finger as shown in shadow) to change the second transmission position of the first ultrasound signal.

As illustrated in FIG. 6B, the ultrasound apparatus 1000 may change the second transmission position of the first ultrasound signal on the basis of a user input for moving the second indicator 602. The ultrasound apparatus 1000 may sequentially transmit the first ultrasound signal (the push ultrasound signal) from the first transmission position and the changed second transmission position to generate a new shear wave in an object. In this case, since the lesion-suspected region 610 is not under the second indicator 602, the shear wave is well propagated to the lesion-suspected region 610.

The ultrasound apparatus 1000 may trace the second ultrasound signal (the trace ultrasound signal) by using the newly generated shear wave to generate a new elastography image 600-2. The ultrasound apparatus 1000 may display the new elastography image 600-2, the first indicator 601 corresponding to the first transmission position of the first ultrasound signal, and the second indicator 602 corresponding to the changed second transmission position of the first ultrasound signal. In comparison with the first elastography image 600-1, an elastography image value of the lesion-suspected region 610 is accurate in the new elastography image 600-2.

According to an embodiment, the ultrasound apparatus 1000 may provide information about the transmission position of the first ultrasound signal, thereby enabling the user to check a degree of accuracy of each region of an elastography image and enabling the user to change the transmission position of the first ultrasound signal through simple user manipulation.

In FIGS. 6A and 6B, the indicator indicating the transmission position of the first ultrasound signal is displayed as a triangular icon, but is not limited thereto. The indicator may have various shapes.

Figure 7:
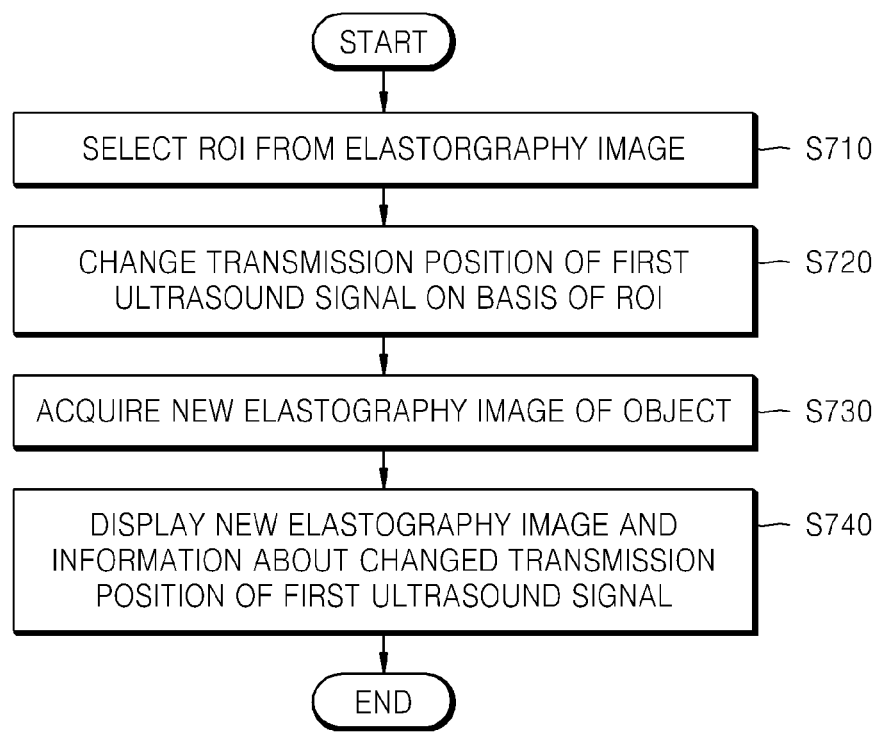
FIG. 7 is a flowchart for describing a method of changing the transmission position of a first ultrasound signal on the basis of an ROI, according to an embodiment.

FIG. 7 is a flowchart for describing a method of changing the transmission position of a first ultrasound signal on the basis of an ROI (Region of Interest), according to an embodiment.

In operation S710, the ultrasound apparatus 1000 may select an ROI from an elastography image.

According to an embodiment, the ultrasound apparatus 1000 may select the ROI from the elastography image on the basis of a user input. For example, the ultrasound apparatus 1000 may receive a user input for selecting the ROI from the elastography image. The ROI may include at least one of a cystis image and a tumor image, but is not limited thereto.

Here, the user input for selecting the ROI may be various. For example, a user may select the ROI by using a directional key, a trackball, a mouse, a touch, a voice, or the like, but is not limited thereto.

According to another embodiment, the ultrasound apparatus 1000 may automatically select the ROI. In an elastography image using a shear wave, an absolute elasticity value (for example, a shear modulus) based on a shear-wave speed is provided, and thus, the ultrasound apparatus 1000 may automatically select the ROI by using the absolute elasticity value (for example, the shear modulus).

For example, the ultrasound apparatus 1000 may select, as the ROI, a region of which the shear modulus is equal to or more than 20 kPa. Also, the ultrasound apparatus 1000 may select, as the ROI, a rectangular region wholly including red.

In operation S720, the ultrasound apparatus 1000 may change the transmission position of the first ultrasound signal on the basis of the selected ROI. According to an embodiment, the ultrasound apparatus 1000 may change the transmission position of the first ultrasound signal in order for the first ultrasound signal to be transmitted to a region other than the ROI of the object. For example, when the position of the probe 1010 is fixed, the ultrasound apparatus 1000 may change a channel, through which the first ultrasound signal is transmitted, from the first channel group to the second channel group.

In operation S730, the ultrasound apparatus 1000 may acquire a new elastography image of the object.

In operation S740, the ultrasound apparatus 1000 may display the new elastography image and information about the changed transmission position of the first ultrasound signal. Operations S730 and S740 respectively correspond to operations S540 and S550 of FIG. 5, and thus, their detailed descriptions are not provided.

Figure 8A:
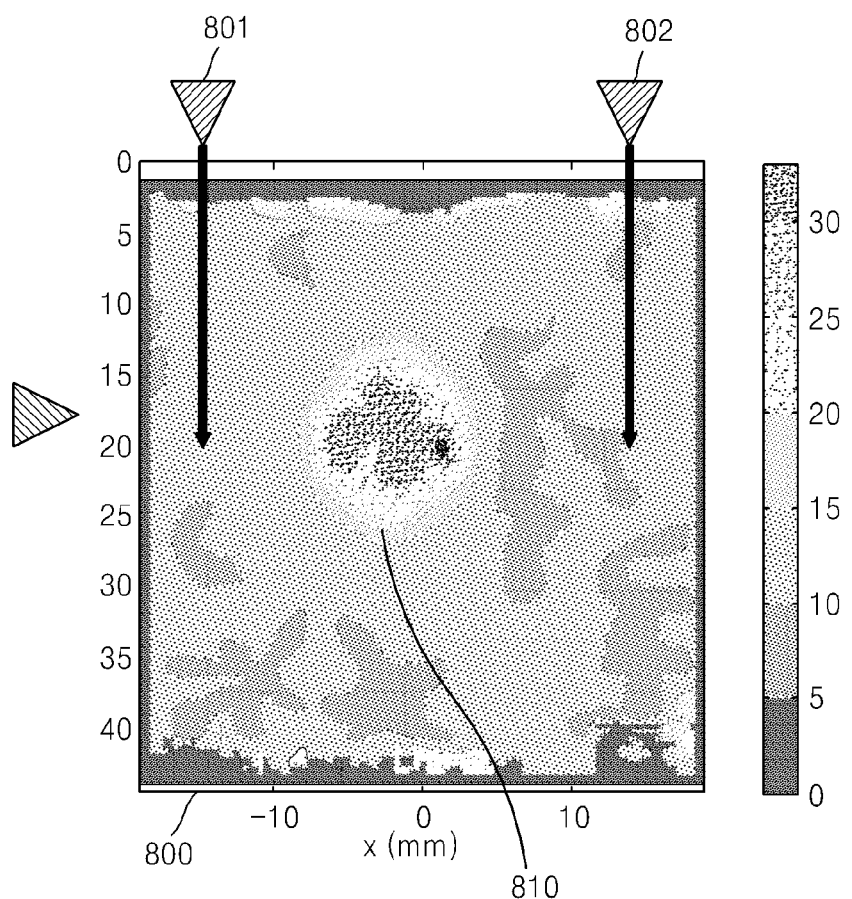
FIGS. 8A to 8C are diagrams for describing an operation that selects an ROI on the basis of a user input and changes a transmission position of a first ultrasound signal on the basis of the selected ROI, according to an embodiment.
Figure 8B:
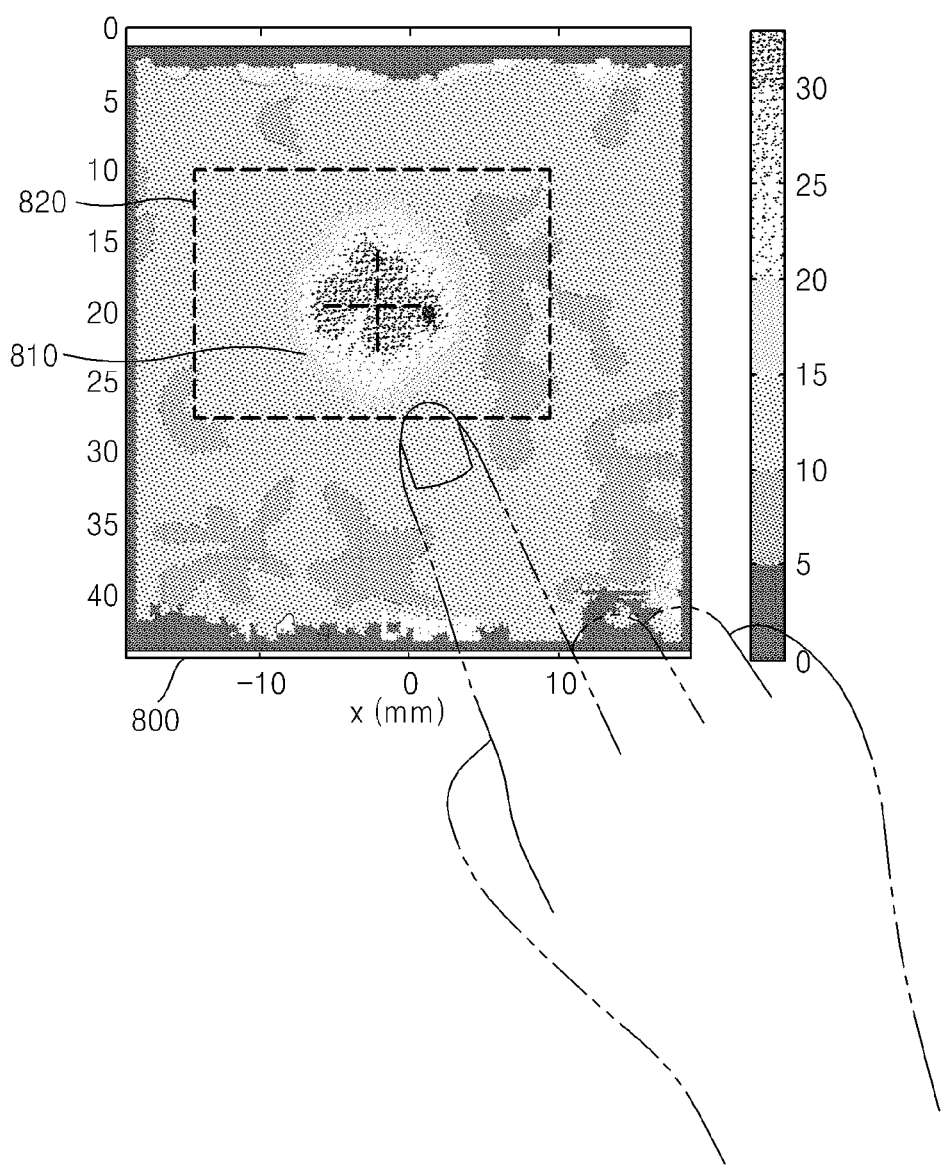
Figure 8C:
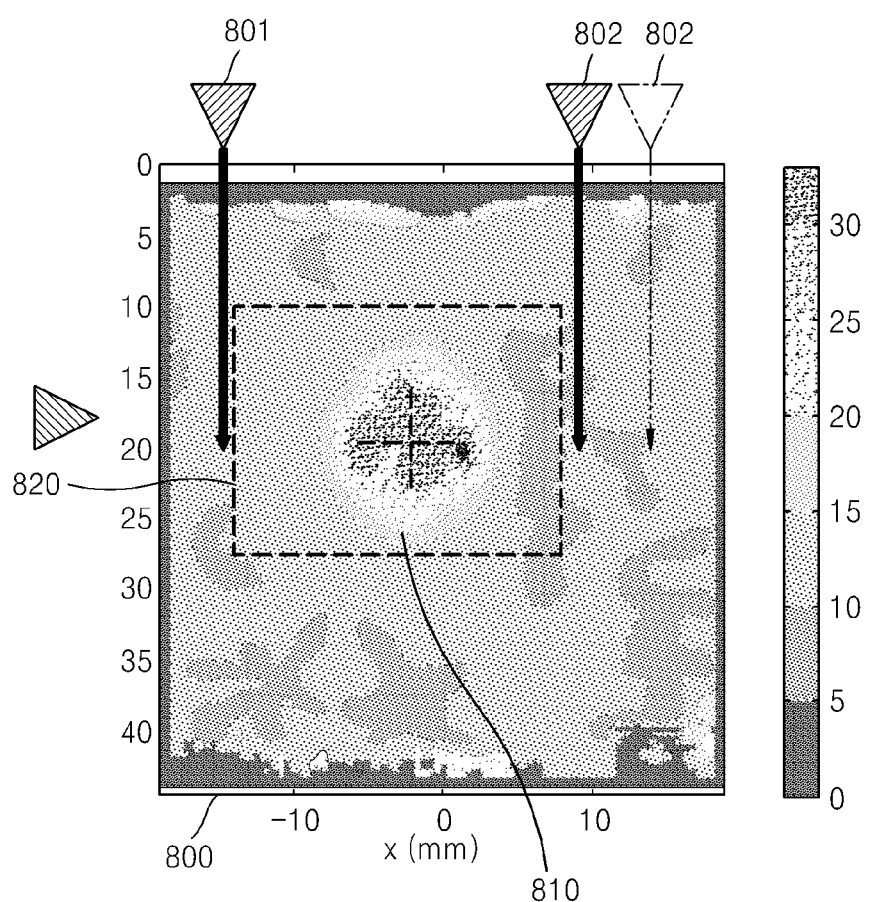

FIGS. 8A to 8C are diagrams for describing an operation that selects an ROI on the basis of a user input and changes a transmission position of a first ultrasound signal on the basis of the selected ROI, according to an embodiment.

As illustrated in FIG. 8A, the ultrasound apparatus 1000 may display an elastography image 800 of an object which is acquired by tracing a shear wave, a first indicator 801 indicating a first transmission position of the first ultrasound signal, and a second indicator 802 indicating a second transmission position of the first ultrasound signal. In this case, a region having a tumor 810 has a shear-wave speed higher than a region having a general tissue, and thus has a high shear modulus.

As illustrated in FIG. 8B, the ultrasound apparatus 1000 may receive selection of an ROI 820 from a user. For example, the user may select, as the ROI 820, a region including the tumor 810.

As illustrated in FIG. 8C, the ultrasound apparatus 1000 may adjust the transmission position of the first ultrasound signal (the push ultrasound signal or beam) on the basis of the ROI 820 selected by the user. For example, the ultrasound apparatus 1000 may automatically adjust the second transmission position of the first ultrasound signal in order for a shear wave to be generated at a predetermined distance (about 1 mm) from the ROI 820. In this case, the second indicator 802 indicating the second transmission position may also be moved and displayed according to the adjusted second transmission position.

The ultrasound apparatus 1000 may again transmit the first ultrasound signal from the adjusted second transmission position to the object, thereby acquiring a new elastography image. In this case, an elasticity value of the ROI 820 of the new elastography image (FIG. 8C) is more accurate than that of the ROI 820 of the previous elastography image 800 (FIG. 8B).

Figure 9A:
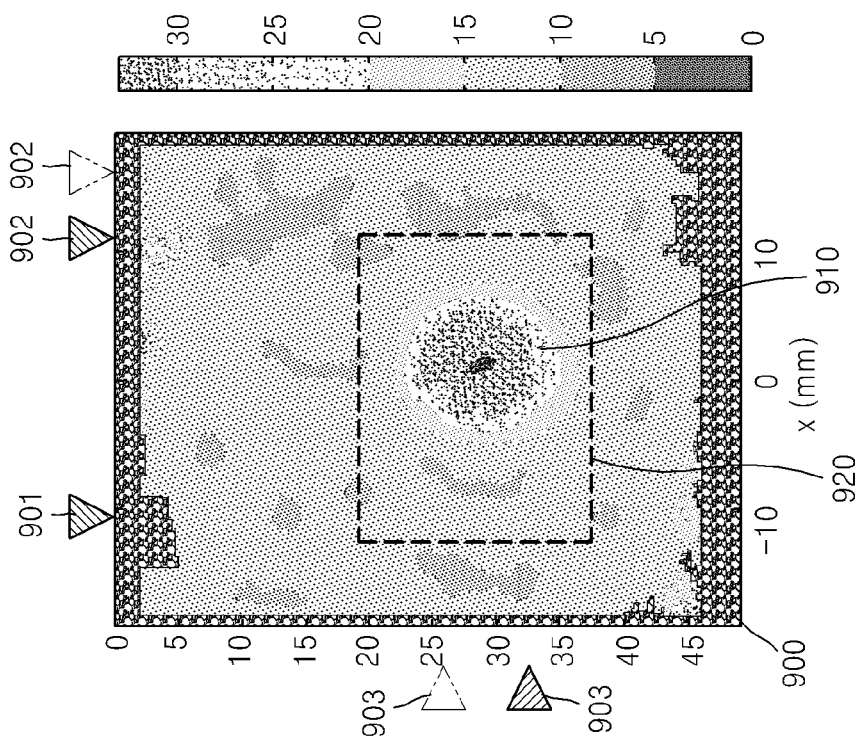
FIGS. 9A and 9B are diagrams for describing an operation in which the ultrasound apparatus according to an embodiment automatically selects an ROI.
Figure 9B:
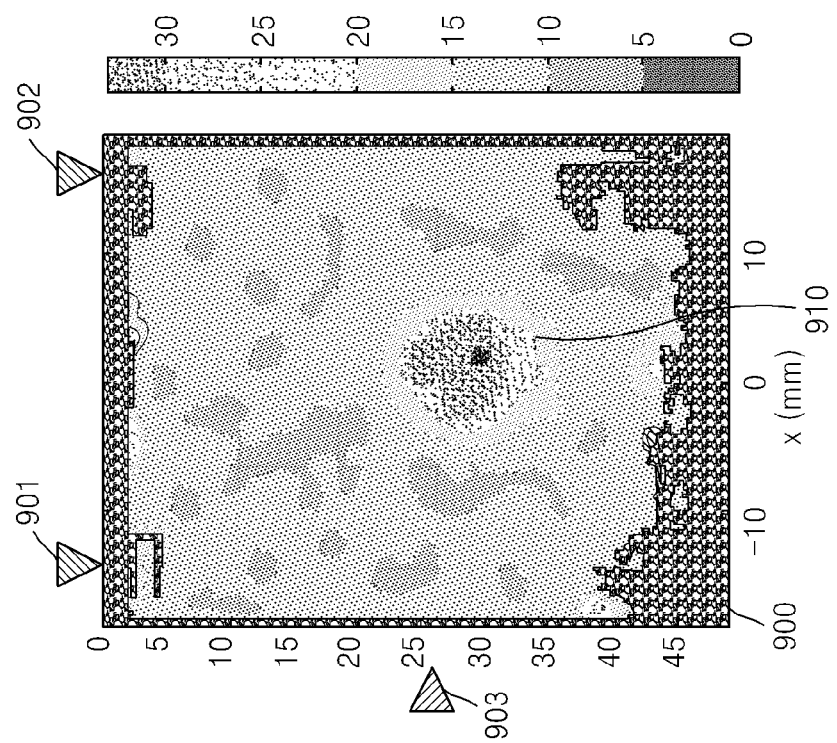

FIGS. 9A and 9B are diagrams for describing an operation in which the ultrasound apparatus according to an embodiment automatically selects an ROI.

As illustrated in FIG. 9A, the ultrasound apparatus 1000 may display an elastography image 900 of an object which is acquired by tracing a shear wave, a first indicator 901 indicating a first transmission position of a first ultrasound signal (a push ultrasound signal), and a second indicator 902 indicating a second transmission position of the first ultrasound signal. Also, the ultrasound apparatus 1000 may display a third indicator 903 indicating a focal depth. In this case, a region having a tumor 910 has a shear-wave speed higher than a region having a general tissue, and thus has a high shear modulus.

As illustrated in FIG. 9B, the ultrasound apparatus 1000 may automatically select an ROI 920 of the elastography image 900. For example, the ultrasound apparatus 1000 may automatically select the ROI 920 including the tumor 910 on the basis of at least one of a shear modulus, a color, and a shear-wave speed of the elastography image 900.

The ultrasound apparatus 1000 may adjust the transmission position of the first ultrasound signal (the push ultrasound signal) on the basis of the ROI 920 selected by the user. For example, the ultrasound apparatus 1000 may automatically adjust the second transmission position of the first ultrasound signal in order for a shear wave to be generated at a predetermined distance (about 1 mm) from the ROI 920. In this case, the second indicator 902 indicating the second transmission position may also be moved and displayed according to the adjusted second transmission position.

Also, the ultrasound apparatus 1000 may adjust a focal depth value on the basis of the ROI 920 selected by the user. In this case, the third indicator 903 indicating the focal depth may also be moved and displayed according to the adjusted focal depth.

Figure 10:
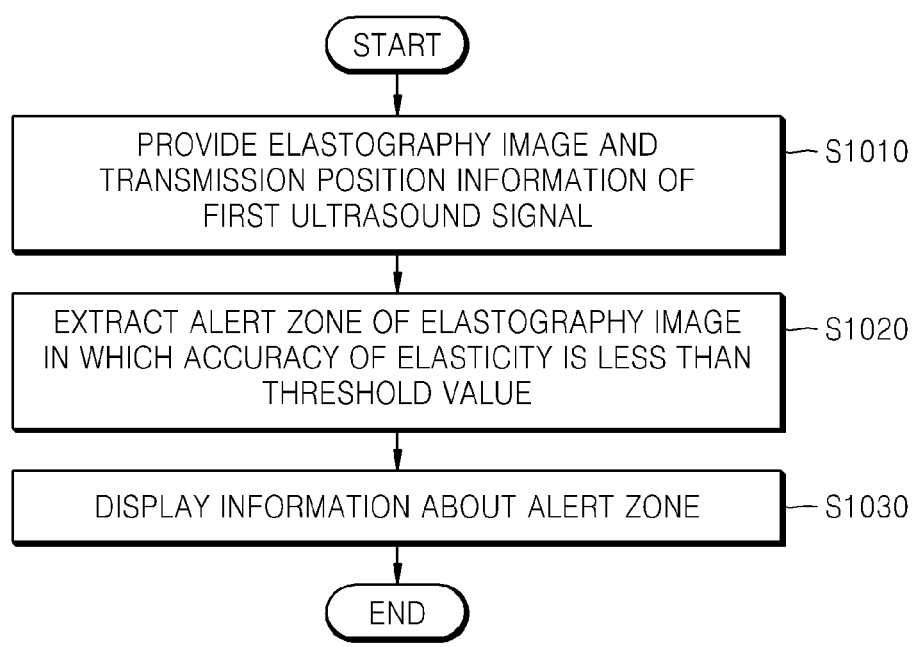
FIG. 10 is a flowchart for describing a method of providing information about an alert zone in which an accuracy of an elasticity value is less than a threshold value, according to an embodiment.

FIG. 10 is a flowchart for describing a method of providing information about an alert zone in which an accuracy of an elasticity value is less than a threshold value, according to an embodiment.

In operation S1010, the ultrasound apparatus 1000 may provide an elastography image of an object and transmission position information of a first ultrasound signal. Operation S1010 corresponds to operation S350 of FIG. 3, and thus, its detailed description is not provided.

In operation S1020, the ultrasound apparatus 1000 may extract an alert zone of the elastography image in which an accuracy of an elasticity value is less than a threshold value, on the basis of the transmission position information of a first ultrasound signal. The elasticity value may be a value that is obtained by digitizing an elasticity of the object. The elasticity value may be expressed as a shear modulus, a shear-wave speed, a color value, etc., but is not limited thereto.

The alert zone may be a region having a high possibility that the elasticity value is not normally calculated. For example, the alert zone may include a region, in which the elasticity value is not calculated, and a region in which the elasticity value is calculated but an accuracy of the elasticity value is less than the threshold value.

According to an embodiment, the ultrasound apparatus 1000 may extract the alert zone of the elastography image in which an accuracy of the elasticity value is less than the threshold value, on the basis of the transmission position information of a first ultrasound signal. For example, a shear wave is not normally propagated to a region on a path through which the first ultrasound signal is transmitted, and thus, the region has an accuracy of the elasticity value less than the threshold value.

According to an embodiment, the ultrasound apparatus 1000 may extract the alter zone in further consideration of the elastography image. For example, the ultrasound apparatus 1000 may extract, as the alert zone, a region of the elastography image for which transparency processing has been performed because the elasticity value is not normally calculated.

In operation S1030, the ultrasound apparatus 1000 may display information about the alert zone. The information about the alert zone may be displayed as various types. For example, the ultrasound apparatus 1000 may display the alert zone in a tetragonal shape, a circular shape, an oval shape, or the like, and add a color to the alert zone. This will be described below in detail with reference to FIG. 11.

Figure 11:
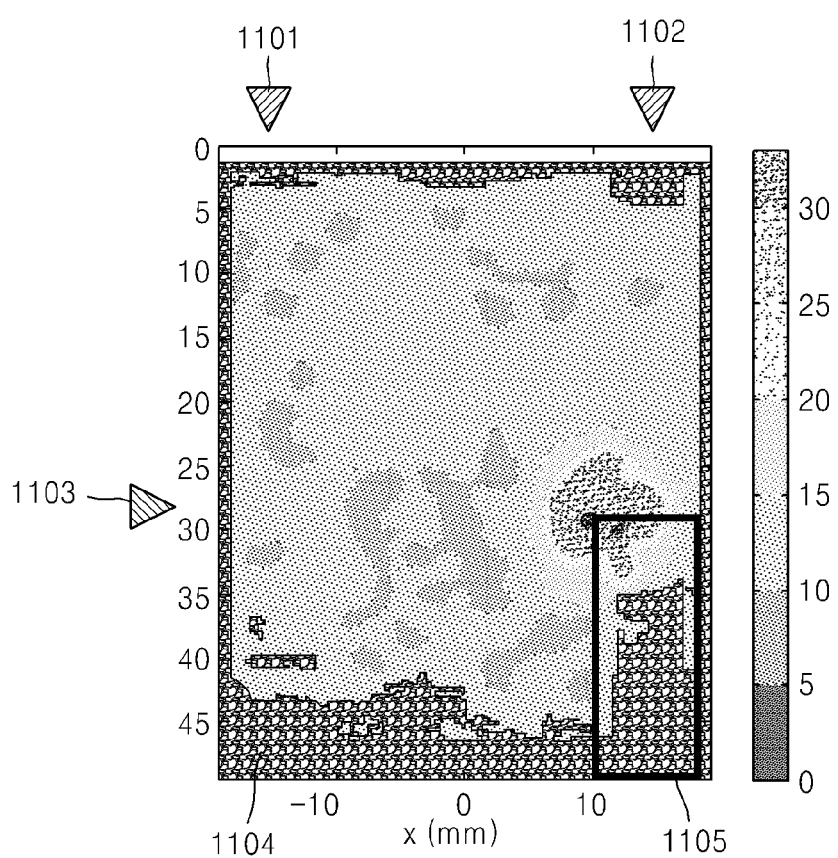
FIG. 11 is a diagram illustrating an example of an alert zone.

FIG. 11 is a diagram illustrating an example of an alert zone.

As illustrated in FIG. 11, the ultrasound apparatus 1000 may display an elastography image of an object, a first indicator 1101 indicating a first transmission position of a first ultrasound signal (a push ultrasound signal), a second indicator 1102 indicating a second transmission position of the first ultrasound signal, and a third indicator 1103 indicating a focal depth of the first ultrasound signal.

The ultrasound apparatus 1000 may display the elastography image to overlap on the B mode image. In this case, the ultrasound apparatus 1000 may perform transparency processing of a region 1104 of the elastography image in which an elasticity value is not calculated. That is, the B mode image may be displayed in the region 1104 in which the elasticity value is not calculated.

Moreover, the ultrasound apparatus 1000 may extract a region having a high possibility that the elasticity value is not normally calculated, in consideration of at least one of the transmission position of the first ultrasound signal, a generation position of a shear wave, and the elastography image. For example, the ultrasound apparatus 1000 may extract an alert zone 1105 in which an accuracy of the elasticity value is less than the threshold value (for example, about 50%). Furthermore, the ultrasound apparatus 1000 displays the alert zone 1105 on the elastography image, thereby minimizing an error when the user diagnoses a lesion.

FIG. 12 is a flowchart for describing a method of providing guide information which guides a movement of the probe, according to an embodiment.

In operation S1210, the ultrasound apparatus 1000 may provide an elastography image of an object and transmission position information of a first ultrasound signal. Operation S1210 corresponds to operation S350 of FIG. 3, and thus, its detailed description is not provided.

In operation S1220, the ultrasound apparatus 1000 may select an ROI from the elastography image.

According to an embodiment, the ultrasound apparatus 1000 may automatically select the ROI from the elastography image. For example, the ultrasound apparatus 1000 may select, as the ROI, a region (for example, a region having a tumor) in which a shear modulus is equal to or greater than a threshold value. Also, according to another embodiment, the ultrasound apparatus 1000 may select the ROI from the elastography image on the basis of a user input.

In operation S1230, the ultrasound apparatus 1000 may provide guide information which guides a movement of the probe 1010, on the basis of information about the ROI. For example, when the ROI is on a moving path of the first ultrasound signal, a shear wave cannot be propagated to or into the ROI. Therefore, the ultrasound apparatus 1000 may provide information about a moving direction of the probe 1010 so that a transmission position (or a generation position of the shear wave) of the first ultrasound signal is outside the ROI. Also, when the ultrasound apparatus 1000 transmits the first ultrasound signal from a plurality of transmission positions, the ultrasound apparatus 1000 may guide the movement of the probe 1010 because the ROI is between the transmission positions.

According to an embodiment, the ultrasound apparatus 1000 may guide the changing of the transmission position of the first ultrasound signal on the basis of the information about the ROI.

FIG. 13 is a diagram illustrating an example of a guide image which guides the movement of the probe.

As illustrated in FIG. 13, the ultrasound apparatus 1000 may display an elastography image of an object, a first indicator 1301 indicating a first transmission position of a first ultrasound signal (a push ultrasound signal), a second indicator 1302 indicating a second transmission position of the first ultrasound signal, and a third indicator 1303 indicating a focal depth of the first ultrasound signal.

The ultrasound apparatus 1000 may select a lesion-suspected region 1310 as an ROI on the basis of a shear modulus or color information. In this case, the lesion-suspected region 1310 is under the second indicator 1302, and thus, the ultrasound apparatus 1000 may determine that an elasticity value of the lesion-suspected region 1310 is not accurate. Therefore, the ultrasound apparatus 1000 may provide guide information 1320 for guiding the movement of the probe 1010 so that the lesion-suspected region 1310 is moved relative to the first and second transmission positions of the first ultrasound signal.

A user may determine that it is required to move the lesion-suspected region 1310 to the left, on the basis of a check result of the guide information 1320. In this case, the user may move the probe 1010, thereby allowing the lesion-suspected region 1310 to be changed relative to the first and second transmission positions of the first ultrasound signal.

Figure 14:
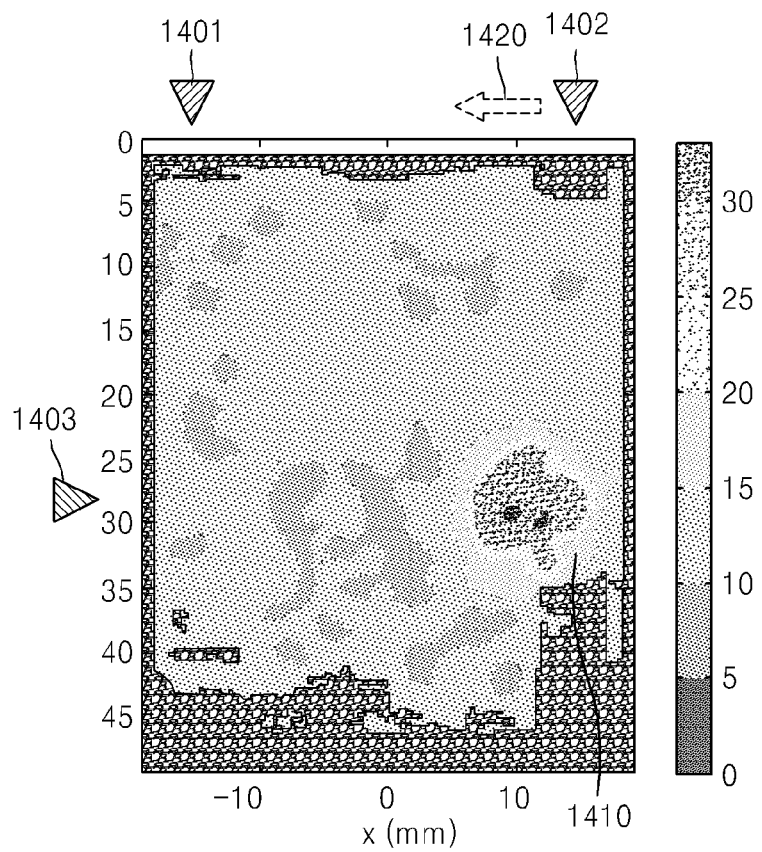
FIG. 14 is a diagram illustrating an example of a guide image which guides the changing of a transmission position of a first ultrasound signal.

FIG. 14 is a diagram illustrating an example of a guide image which guides the changing of a transmission position of a first ultrasound signal.

As illustrated in FIG. 14, the ultrasound apparatus 1000 may display an elastography image of an object, a first indicator 1401 indicating a first transmission position of a first ultrasound signal (a push ultrasound signal), a second indicator 1402 indicating a second transmission position of the first ultrasound signal, and a third indicator 1403 indicating a focal depth of the first ultrasound signal.

The ultrasound apparatus 1000 may select a lesion-suspected region 1410 as an ROI on the basis of a shear modulus or color information. In this case, the lesion-suspected region 1410 is under the second indicator 1402, and thus, the ultrasound apparatus 1000 may determine that an elasticity value of the lesion-suspected region 1410 is not accurate. Therefore, the ultrasound apparatus 1000 may provide guide information 1420 for guiding a movement of the second transmission position so that the lesion-suspected region 1410 is adjusted relative to the first and second transmission positions of the first ultrasound signal. For example, the ultrasound apparatus 1000 may provide information for moving the second indicator 1402 indicating the second transmission position in a left direction.

A user may check the guide information 1420, and move the second indicator 1402 in the left direction. At this point, the ultrasound apparatus 1000 may change the second transmission position of the first ultrasound signal on the basis of the movement of the second indicator 1402.

Figure 15:
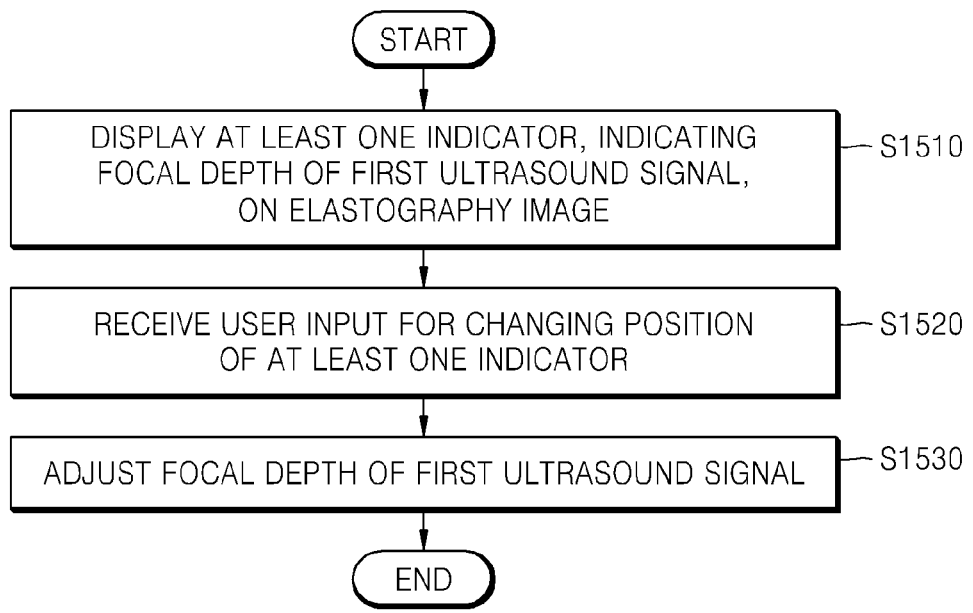
FIG. 15 is a flowchart for describing a method of adjusting a focal length of a first ultrasound signal, according to an embodiment.

FIG. 15 is a flowchart for describing a method of adjusting a focal length of a first ultrasound signal, according to an embodiment.

In operation S1510, the ultrasound apparatus 1000 may display at least one indicator, indicating a focal depth of the first ultrasound signal, on an elastography image. The focal depth may denote a position on which the first ultrasound signal focuses. Here, the at least one indicator indicating the focal depth may be displayed as various types. For example, the indicator may be displayed as an arrow, a line, a box, a circle, or the like, but is not limited thereto.

In operation S1520, the ultrasound apparatus 1000 may receive a user input for changing a position of the at least one indicator indicating the focal depth of the first ultrasound signal. Here, the user input may be various. For example, the user input may include a key input, a touch input, a voice input, a motion input, and a multi-input, but is not limited thereto.

In operation S1530, the ultrasound apparatus 1000 may adjust a focal depth of the first ultrasound signal on the basis of the user input. This will be described in detail with reference to FIGS. 16A and 16B.

Figure 16B:
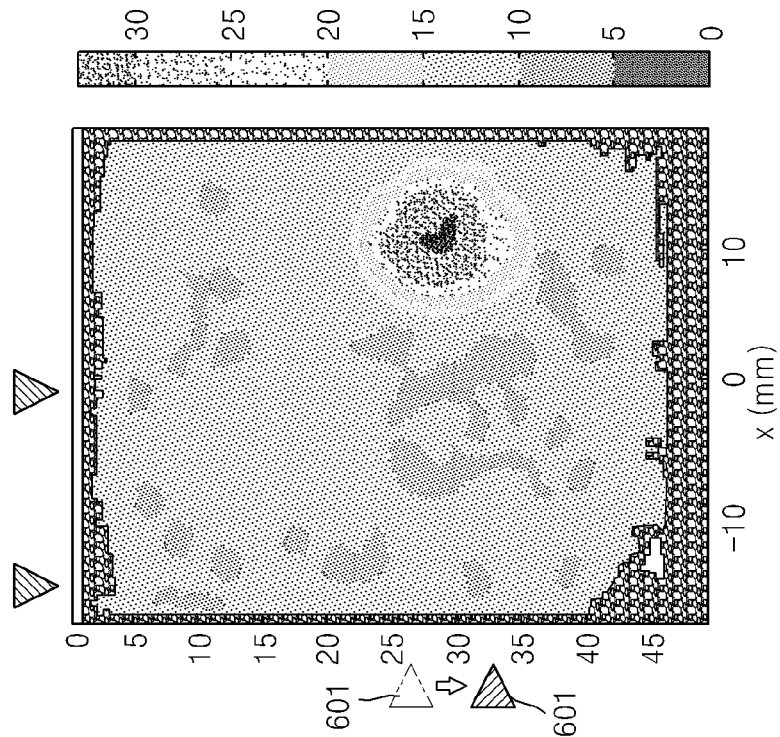
FIGS. 16A and 16B are diagrams for describing an operation in which the ultrasound apparatus according to an embodiment adjusts a focal depth on the basis of a user input.
Figure 16A:
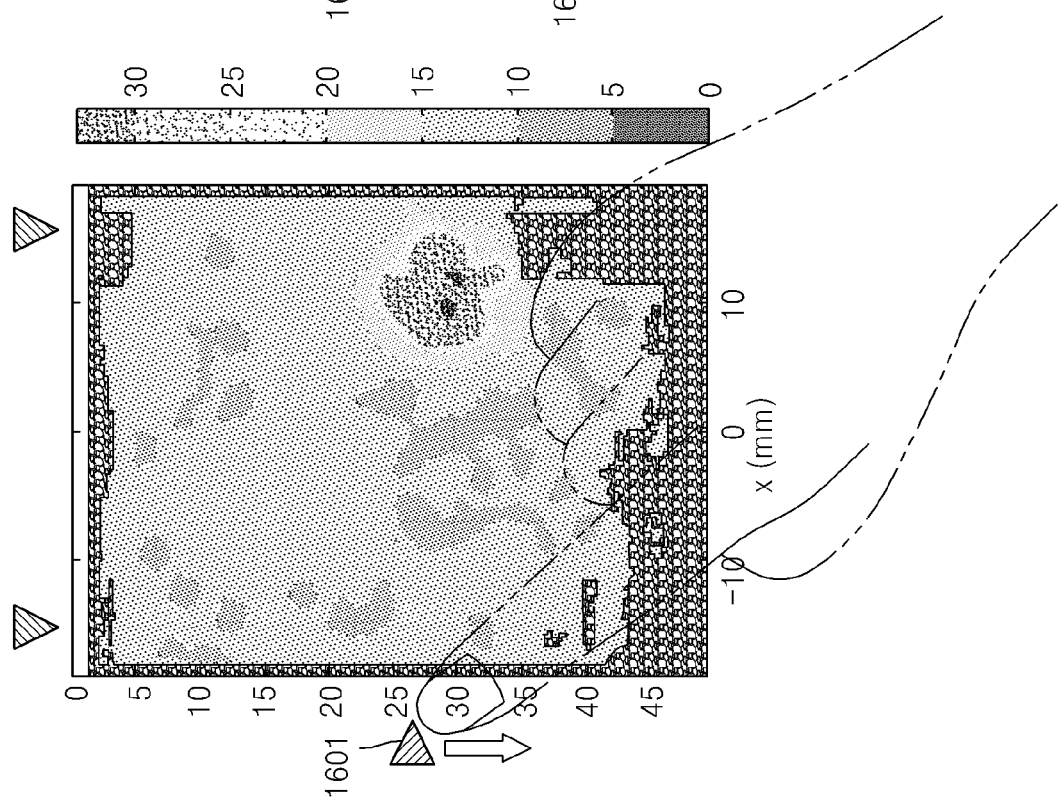

FIGS. 16A and 16B are diagrams for describing an operation in which the ultrasound apparatus according to an embodiment adjusts a focal depth on the basis of a user input.

As illustrated in FIG. 16A, the ultrasound apparatus 1000 may display an elastography image of an object and an indicator 1601 indicating a focal depth of a first ultrasound signal (a push ultrasound signal). In this case, the user may move the indicator 1601.

As illustrated in FIG. 16B, the ultrasound apparatus 1000 may adjust the focal depth of the first ultrasound signal on the basis of the movement of the indicator 1601. The ultrasound apparatus 1000 may transmit the first ultrasound signal to the object according to the adjusted focal depth. At this point, a new shear wave may be generated in the object. The ultrasound apparatus 1000 may trace the new shear wave by using a second ultrasound signal, and generate the new elastography image by using speed information of the new shear wave.

Figure 17:
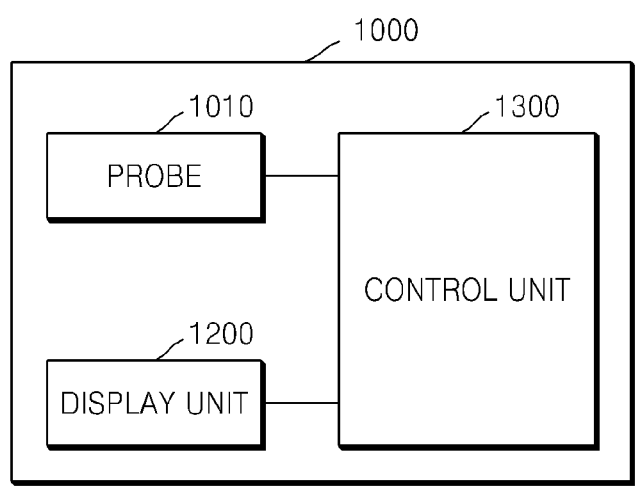
FIGS. 17 and 18 are block diagrams for describing a configuration of the ultrasound apparatus according to an embodiment.
Figure 18:
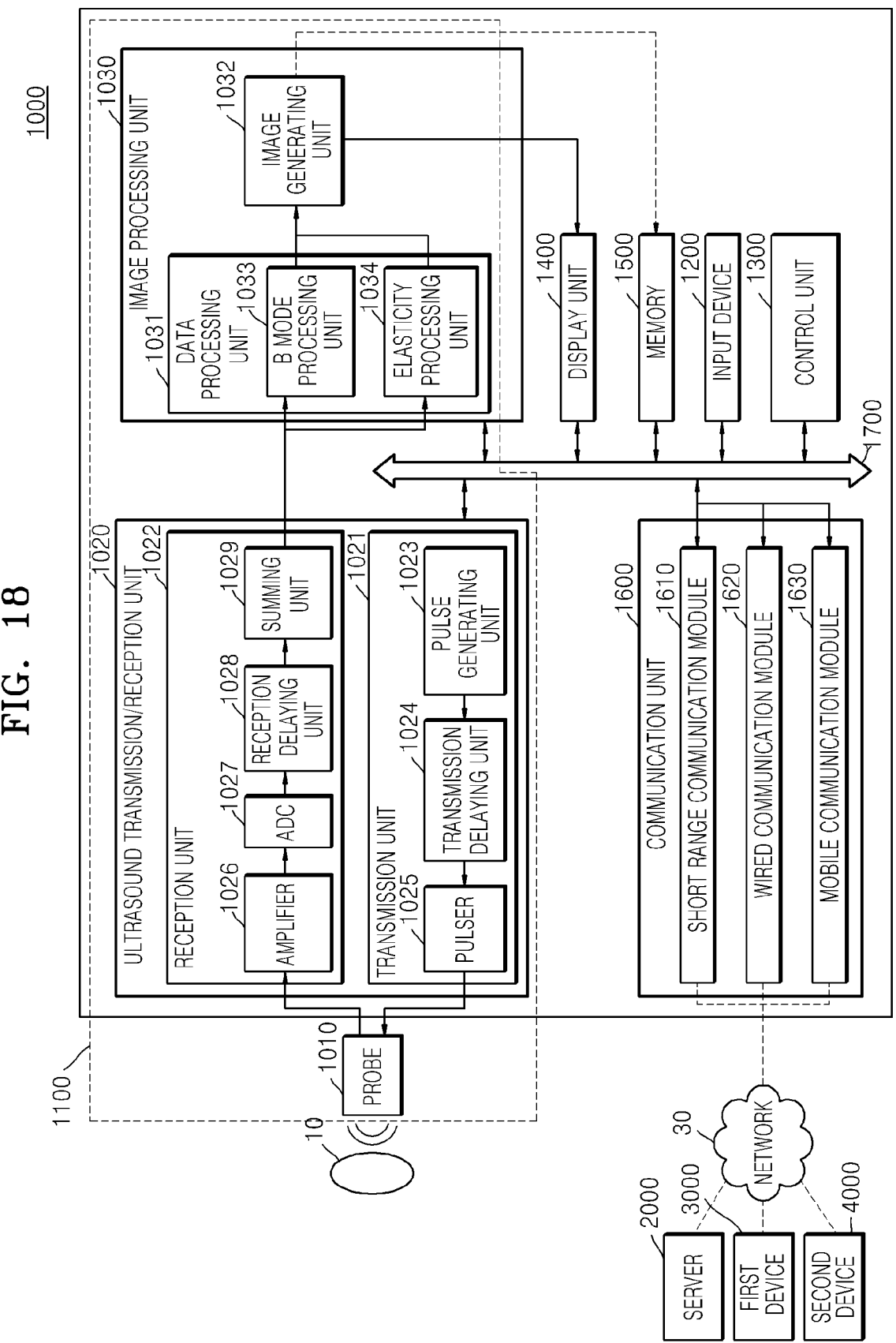

FIGS. 17 and 18 are block diagrams for describing a configuration of the ultrasound apparatus according to an embodiment.

As illustrated in FIG. 17, the ultrasound apparatus 1000 according to an embodiment may include the probe 1010, a display unit 1200, and a control unit 1300. However, only some of the elements are essential elements. The ultrasound apparatus 1000 may include additional elements, in addition to the illustrated elements. Alternatively, the ultrasound apparatus 1000 may include elements less than the number of the illustrated elements.

For example, as illustrated in FIG. 18, the ultrasound apparatus 1000 according to an embodiment may include an ultrasound image acquiring unit 1100, a display unit 1200, a control unit 1300, a user input unit 1400, a communication unit 1500, and a memory 1600. Here, the above-described elements may be connected to one another via a bus 1700.

Hereinafter, the elements will be sequentially described in detail.

The ultrasound image acquiring unit 1100 may acquire ultrasound image data of the object 10. The ultrasound image data according to an embodiment may be two-dimensional (2D) or three-dimensional (3D) ultrasound image data of the object 10.

According to an embodiment, the ultrasound image acquiring unit 1100 may include the probe 1010, an ultrasound transmission/reception unit 1020, and an image processing unit 1030.

The probe 1010 transmits ultrasound waves to the object 10 based on a driving signal applied by the ultrasound transmission/reception unit 1020 and receives echo signals reflected by the object 10. The probe 1010 includes a plurality of transducers, and the plurality of transducers oscillate based on electric signals transmitted thereto and generate acoustic energy, that is, ultrasound waves. Furthermore, the probe 1010 may be connected to the main body of the ultrasound apparatus 1000 wiredly or wirelessly. According to embodiments, the ultrasound apparatus 1000 may include a plurality of the probes 1010. According to an embodiment, the probe 1010 may include at least one of a 1D probe, a 1.5D probe, a 2D (matrix) probe, and a 3D probe.

According to an embodiment, the probe 1010 may transmit the first ultrasound signal pushing the object 10 to the object 10, thereby inducing a shear wave where shear is the chance of shape, without change of volume, of a layer of the substance, produced by a pair of equal forces acting in opposite directions along the two faces of the layer. The probe 1010 may transmit the second ultrasound signal tracing the shear wave to the object 10, and receive a response signal to the second ultrasound signal from the object 10.

A transmission unit 1021 supplies a driving signal to the probe 1010 and includes a pulse generating unit 1023, a transmission delaying unit 1024, and a pulser 1025. The pulse generating unit 1023 generates pulses for forming transmission ultrasound waves based on a predetermined pulse repetition frequency (PRF), and the transmission delaying unit 1024 applies a delay time for determining transmission directionality to the pulses. Pulses to which a delay time is applied correspond to a plurality of piezoelectric vibrators included in the probe 1010, respectively. The pulser 1025 applies a driving signal (or a driving pulse) to the probe 1010 as a timing corresponding to each pulse to which a delay time is applied.

A reception unit 1022 generates ultrasound data by processing echo signals received from the probe 1010 and may include an amplifier 1026, an analog-digital converter (ADC) 1027, a reception delaying unit 1028, and a summing unit 1029. The amplifier 1026 amplifies echo signals in each channel, and the ADC 1027 analog-digital converts the amplified echo signals. The reception delaying unit 1028 applies delay times for determining reception directionality to the digital-converted echo signals, and the summing unit 1029 generates ultrasound data by summing the echo signals processed by the reception delaying unit 1028. Also, according to embodiments, the reception unit 1022 may not include the amplifier 1026.

The image processing unit 1030 generates an ultrasound image by scan-converting ultrasound data generated by the ultrasound transmission/reception unit 1020 and displays the ultrasound image. Meanwhile, an ultrasound image may include not only a grayscale ultrasound image obtained by scanning an object in an amplitude (A) mode, a brightness (B) mode, and a motion (M) mode, but also a blood flow Doppler image showing flow of blood (aka a color Doppler image), a tissue Doppler image showing movement of tissues, and a spectral Doppler image showing moving speed of an object as a waveform.

A B mode processing unit 1033 extracts B mode components from ultrasound data and processes the B mode components. An image generating unit 1032 may generate an ultrasound image indicating signal intensities as brightness based on the extracted B mode components.

Similarly, the elasticity processing unit 1034 extracts a shear-wave speed component (for example, a shear modulus) from elasticity data to process the shear-wave speed. The image generating unit 1032 may an elastography in which the shear-wave speed is expressed as a color, on the basis of the shear-wave speed component (for example, the shear modulus) extracted by the elasticity processing unit 1034.

Moreover, a Doppler processing unit (not shown) may extract Doppler components from ultrasound data, and the image generating unit 1032 may generate a Doppler image indicating movement of an object as colors or waveforms based on the extracted Doppler components.

The image generating unit 1032 according to an embodiment may generate a 3D ultrasound image via volume-rendering of volume data and may also generate an elastrography which visualizes deformation of the object 10 due to a pressure.

Furthermore, the image generating unit 1032 may display various pieces of additional information in an ultrasound image by using texts and graphics. For example, the image generating unit 1032 may add at least one annotation, associated with all or a portion of an ultrasound image, to the ultrasound image. That is, the image generating unit 1032 may analyze the ultrasound image, and recommend the at least one annotation associated with all or a portion of an ultrasound image, on the basis of the analysis result. Also, the image generating unit 1032 may add additional information, corresponding to an ROI selected by a user, to the ultrasound image.

The image processing unit 1030 may extract an ROI from the ultrasound image by using an image processing algorithm. For example, the image processing unit 1030 may extract an ROI from an elastography image on the basis of a shear wave. In this case, the image processing unit 1030 may add a color, a pattern, or a border to the ROI.

The display unit 1200 displays and outputs information obtained through processing by the ultrasound apparatus 1000. For example, the display unit 1200 may display the ultrasound image, or display a user interface (UI) or a graphics user interface (GUI) relating to a control panel.

The display unit 1200 may provide the elastography image of the object 10 and the transmission position information of the first ultrasound signal. For example, the display unit 1200 may display at least one indicator, indicating the transmission position of the first ultrasound signal, on the elastography image. Also, the display unit 1200 may display a new elastography image and information about a changed transmission position of the first ultrasound signal.

The display unit 1200 may further provide information about a focal depth of the first ultrasound signal. For example, the display unit 1200 may display at least one indicator, indicating the focal depth of the first ultrasound signal, on the elastography image.

The display unit 1200 may display an alert zone of the elastography image, in which an accuracy of an elasticity value is less than the threshold value, on the elastography image. Also, the display unit 1200 may display guide information for guiding a movement of the probe 1010.

When the display unit 1200 is configured with a touch screen in which a touch pad forms a layer structure, the display unit 1200 may be used as an input device in addition to an output device. The display unit 1200 may include at least one of a liquid crystal display (LCD), a thin film transistor-liquid crystal display, an organic light-emitting diode (OLED) display, a flexible display, a 3D display, and an electrophoretic display. The ultrasound apparatus 1000 may include two or more the display units 1200 depending on an implementation type of the ultrasound apparatus 1000.

The control unit 1300 controls an overall operation of the ultrasound apparatus 1000. For example, the control unit 1300 may overall control the ultrasound image acquiring unit 1100, the display unit 1200, the user input unit 1400, the communication unit 1500, and the memory 1600.

The control unit 1300 may acquire the elastography image of the object 10 on the basis of a response signal to the second ultrasound signal. The control unit 1300 may control the probe 1010 so as to change the transmission position of the first ultrasound signal, on the basis of a user input. When the transmission position of the first ultrasound signal is changed, the control unit 1300 may acquire a new elastography image of the object 10.

The control unit 1300 may select an ROI from the elastography image. For example, the control unit 1300 may select the ROI from the elastography image according to a user input, or may automatically select the ROI.

The control unit 1300 may change the transmission position of the first ultrasound signal on the basis of the selected ROI to acquire a new elastography image. For example, the control unit 1300 may change the transmission position of the first ultrasound signal in order for the first ultrasound signal to be transmitted to a region other than the ROI of the object 10.

The control unit 1300 may adjust a focal depth of the first ultrasound signal on the basis of a user input which changes a position of at least one indicator.

The control unit 1300 may select the ROI from the elastography image, and control the display unit 1200 to display guide information which guides a movement of the probe 1010, on the basis of information about the ROI.

Moreover, the control unit 1300 may extract an alert zone of the elastography image in which an accuracy of an elasticity value is less than the threshold value, on the basis of the transmission position information of the first ultrasound signal, and may control the display unit 1200 to display information about the alert zone.

The user input unit 1400 may denote a means that allows a user (for example, a sonographer) to input data used to control the ultrasound apparatus 1000. For example, the user input unit 1400 may include a keypad, a dome switch, a touch pad (for example, of a contact capacitive type, a press resistive type, an infrared sensing type, a surface ultrasonic conductive type, an integration tension measurement type, or a piezo effect type), a jog wheel, and a jog switch, but is not limited thereto. For example, the user input unit 1400 may further include various other input means including an electrocardiogram measuring module, a respiration measuring module, a voice recognition sensor, a gesture recognition sensor, a fingerprint recognition sensor, an iris recognition sensor, a depth sensor, a distance sensor, etc.

According to an embodiment, the user input unit 1400 may detect a proximity touch in addition to a real touch. The user input unit 1400 may detect a touch input (for example, touch & hold, tap, double taps, flick, or the like) for the ultrasound image. Also, the user input unit 1400 may detect a drag input from a position at which a touch input is detected. In addition, the user input unit 1400 may detect multi touch inputs (for example, pinches) for at least one two positions included in the ultrasound image.

The user input unit 1400 may receive a user input which changes a position of at least one indicator corresponding to the transmission position of the first ultrasound signal. Also, the user input unit 1400 may receive a user input which changes a position of an indicator indicating the focal depth of the first ultrasound signal.

The communication unit 1500 may include one or more elements that enable communication between the ultrasound apparatus 1000 and a server 2000, between the ultrasound apparatus 1000 and a first device 3000, and between the ultrasound apparatus 1000 and a second device 4000. For example, the communication unit 1500 may include a short-range communication module 1510, a wired communication module 1520, and a mobile communication module 1530.

The short-range communication module 1510 may refer to a module for close-distance communication within a predetermined distance. Examples of close-distance communication techniques according to an embodiment may include wireless LAN, Wi-Fi, Bluetooth, Zigbee, Wi-Fi Direct (WFD), ultra wideband (UWB), infrared data association (IrDA), Bluetooth Low Energy (BLE), and near field communication (NFC). However, the embodiments are not limited thereto.

The wired communication module 1520 refers to a module for communication using electric signals or optical signals. Examples of wired communication techniques according to an embodiment may include a pair cable, a coaxial cable, an optical fiber cable, and an Ethernet cable.

The mobile communication module 1530 transmits and receives wireless signals with at least one of a base station, external devices (for example, the first device 3000 and the second device 4000), and the server 2000 over a mobile communication network. Here, the wireless signals may include voice call signals, video call signals, or various types of data for transmission and reception of text/multimedia messages.

The communication unit 1500 is wiredly or wirelessly connected to a network 30 and communicates with an external device or a server. The communication unit 1500 may exchange data with a hospital server or another medical device in a hospital that is connected with a picture archiving and communications system (PACS). Furthermore, the communication unit 1500 may perform data communication according to the digital imaging and communications in medicine (DICOM) standard.

The communication unit 1500 may transmit and receive data related to diagnosis of an object, e.g., an ultrasound image, ultrasound data, and Doppler data of the object, via the network 30 and may also transmit and receive medical images obtained via other medical devices, e.g., a CT image, a MR image, and an X-ray image. Furthermore, the communication unit 1500 may receive information related to diagnosis history or treatment schedule of a patient from a server and utilizes the information for diagnosing the patient.

The memory 1600 may store a program for processing of the control unit 1300, and store input/output data (for example, ultrasound image data, elasticity data, information about an ROI, an ultrasound image, examinee information, probe information, a body marker, additional information, etc.).

The memory 1600 may include at least one type of storage medium of a flash memory, a hard disk, a multimedia micro card, a card type memory (a secure digital (SD) card, an extreme digital (XD) card, or the like), a random access memory (RAM), a static random access memory (SRAM), a read-only memory (ROM), an electrically erasable programmable read-only memory (EEPROM), and a programmable read-only memory (PROM). Also, the ultrasound apparatus 1000 may use a web storage or a cloud server which performs a storage function of the memory 1600 on the Web.

The method according to the embodiments may be implemented as computer readable code in a computer readable medium. The computer readable recording medium may include a program instruction, a local data file, a local data structure, or a combination thereof. The computer readable recording medium may be specific to exemplary embodiments or commonly known to those of ordinary skill in computer software. The computer readable recording medium includes all types of recordable media in which computer readable data are stored. Examples of the computer readable recording medium include a magnetic medium, such as a hard disk, a floppy disk and a magnetic tape, an optical medium, such as a CD-ROM and a DVD, a magneto-optical medium, such as a floptical disk, and a hardware memory, such as a ROM, a RAM and a flash memory, specifically configured to store and execute program instructions. Furthermore, the computer readable recording medium may be implemented in the form of a transmission medium, such as light, wire or waveguide, to transmit signals which designate program instructions, local data structures and the like. Examples of the program instruction include machine code, which is generated by a compiler, and a high level language, which is executed by a computer using an interpreter and so on.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope as defined by the following claims.

What is claimed is:

1. An apparatus for providing an ultrasound elastography image, the apparatus comprising:
a probe configured to transmit an ultrasound signal into an object, and to receive a response signal;
a controller configured to acquire an elastography image of the object, based on the response signal; and
a display,
wherein the controller is further configured to:
control the probe to transmit a first ultrasound push beam into the object from a first transmission position and a second transmission position, to induce a first pair of shear waves therefrom,
control the probe to transmit a first ultrasound scan signal into the object tracing the first pair of shear waves, and to receive a first response signal to the first ultrasound scan signal,
acquire a first elastography image of the object based on the first response signal,
control the display to display the first elastography image, a first indicator indicating the first transmission position, and a second indicator indicating the second transmission position,
select a region of interest (ROI), having a location, from the first elastography image,
adjust the second transmission position based on the location of the selected ROI, wherein the second transmission position is adjusted relative to the location of the selected ROI and the first transmission position such that the selected ROI is located between the first transmission position and the adjusted second transmission position,
control the display to adjust a position of the second indicator on the display according to the adjusted second transmission position,
control the probe to transmit a second ultrasound push beam into the object from the first transmission position and the adjusted second transmission position, to induce a second pair of shear waves therefrom,
control the probe to transmit a second ultrasound scan signal tracing the second pair of shear waves, and to receive a second response signal to the second ultrasound scan signal from the object, and
acquire a second elastography image based on the second response signal.

2. The apparatus of claim 1, wherein the display is further configured to display guide information for guiding movement of the second transmission position based on the location of the selected ROI.

3. The apparatus of claim 2, further comprising a user input device configured to receive a user input that adjusts the position of the second indicator on the display according to the guide information,
wherein the controller is further configured to adjust the second transmission position based on the user input.

4. The apparatus of claim 3, wherein the display is configured to display the second elastography image, the first indicator indicating the first transmission position, and the user-adjusted second indicator indicating the user-adjusted second transmission position.

5. The apparatus of claim 1, wherein the controller is configured to select the ROI from the first elastography image, based on a user input.

6. The apparatus of claim 1, wherein the probe is further configured to focus the first ultrasound push beam at a focal depth, and the display is further configured to display information about the focal depth of the first ultrasound push beam.

7. The apparatus of claim 6, wherein,
the display is configured to display the information about the focal depth of the first ultrasound push beam by displaying at least one focal depth indicator, indicating the focal depth of the first ultrasound push beam, on the first elastography image, and
wherein the controller is further configured to receive a user input that adjusts a position of the at least one focal depth indicator, and to adjust the focal depth of the first ultrasound push beam, based on the user input.

8. The apparatus of claim 1, wherein the first elastography image comprises a plurality of elasticity values, and
wherein the controller is further configured to:
extract an alert zone from the first elastography image in which an accuracy of an elasticity value of the plurality of elasticity values is less than a threshold value, based on the first transmission position, and
control the display to display information about the alert zone.

9. An apparatus for providing an ultrasound elastography image, the apparatus comprising:
a probe configured to transmit an ultrasound signal into an object, and to receive a response signal;
a controller configured to acquire an elastography image of the object, based on the response signal; and
a display,
wherein the controller is further configured to:
control the probe to transmit a first ultrasound push beam into the object from a first transmission position and a second transmission position, to induce a first pair of shear waves therefrom,
control the probe to transmit a first ultrasound scan signal into the object tracing the first pair of shear waves, and to receive a first response signal to the first ultrasound scan signal,
acquire a first elastography image of the object based on the first response signal,
control the display to display the first elastography image, a first indicator indicating the first transmission position, and a second indicator indicating the second transmission position,
select a region of interest (ROI), having a location, from the elastography image,
adjust the second transmission position based on the location of the selected ROI, wherein the second transmission position is adjusted relative to the location of the selected ROI and the first transmission position such that the selected ROI is located between the first transmission position and the adjusted second transmission position,
control the display to adjust a position of the second indicator on the display according to the adjusted second transmission position,
acquire a new elastography image of the object using a second ultrasound push beam transmitted into the object from the first transmission position and the adjusted second transmission position, and
control the display to display the new elastography image and information about the adjusted second transmission position.

* * * * *